US010617759B2

(12) United States Patent
Han et al.

(10) Patent No.: US 10,617,759 B2
(45) Date of Patent: Apr. 14, 2020

(54) LIGHT-STIMULATED RELEASE OF CARGO FROM OLIGONUCLEOTIDES

(71) Applicant: Trustees of Boston University, Boston, MA (US)

(72) Inventors: Xue Han, Brookline, MA (US); Richie E. Kohman, Cambridge, MA (US); Susie S. Cha, Boston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 16/081,526

(22) PCT Filed: Mar. 1, 2017

(86) PCT No.: PCT/US2017/020167
§ 371 (c)(1),
(2) Date: Aug. 31, 2018

(87) PCT Pub. No.: WO2017/151748
PCT Pub. Date: Sep. 8, 2017

(65) Prior Publication Data
US 2019/0008963 A1   Jan. 10, 2019

Related U.S. Application Data

(60) Provisional application No. 62/301,840, filed on Mar. 1, 2016.

(51) Int. Cl.
| | | |
|---|---|---|
| *C07H 21/00* | (2006.01) | |
| *A61K 41/00* | (2020.01) | |
| *A61N 5/06* | (2006.01) | |
| *A61K 47/54* | (2017.01) | |
| *C07C 247/10* | (2006.01) | |

(52) U.S. Cl.
CPC ........ *A61K 41/0042* (2013.01); *A61K 47/542* (2017.08); *A61K 47/549* (2017.08); *A61N 5/062* (2013.01); *C07C 247/10* (2013.01); *C07H 21/00* (2013.01); *A61N 2005/0661* (2013.01)

(58) Field of Classification Search
None
See application file for complete search history.

(56) References Cited

U.S. PATENT DOCUMENTS

| | | | |
|---|---|---|---|
| 6,384,264 B1 | 5/2002 | dos Santos Cristiano et al. | |
| 2008/0177053 A1 | 7/2008 | Matsuura et al. | |
| 2011/0151451 A1* | 6/2011 | Lemaire | G01N 33/6851 435/6.11 |
| 2013/0171461 A1 | 7/2013 | Dach et al. | |
| 2014/0186875 A1 | 7/2014 | Dratz et al. | |
| 2014/0255307 A1 | 9/2014 | Ahn et al. | |
| 2014/0308234 A1* | 10/2014 | Johnson | C07F 15/0093 424/78.22 |
| 2015/0238516 A1 | 8/2015 | Dowdy et al. | |
| 2016/0169903 A1 | 6/2016 | Dai et al. | |

FOREIGN PATENT DOCUMENTS

| | | |
|---|---|---|
| WO | WO-2015/012912 A2 | 1/2015 |
| WO | WO-2015/057511 A1 | 4/2015 |

OTHER PUBLICATIONS

Zhou et al. Molecular Biosystems 2012, vol. 8, pp. 2395-2404.*
Banerjee et al., "Controlled release of encapsulated cargo from a DNA icosahedron using a chemical trigger," Angew Chem int Ed Engl. 52(27): 6854-7 (2013) (Abstract only).
Chang et al., "A photo-cleavable biotin affinity tag for the facile release of a photo-crosslinked carbohydrate-binding protein," Bioorg Med Chem. 24(6): 1216-24 (2016).
Derr et al., "Tug of war in motor protein ensembles revealed with a programmable DNA origami scaffold," Available in PMC Nov. 26, 2013, published in final edited form as: Science. 338(6107): 662-5 (including Supplementary Materials) (2012) (55 pages).
Douglas et al., "Self-assembly of DNA into nanoscale three-dimensional shapes," Nature. 459(7245): 414-8 (2009).
Ellis-Davies. "Caged compounds: photorelease technology for control of cellular chemistry and physiology," Nat Methods. 4(8): 619-28 (2007).
International Search Report and Written Opinion for International Application No. PCT/US17/20167, dated May 31, 2017 (12 pages).
Kohman et al., "Light sensitization of DNA nanostructures via incorporation of photo-cleavable spacers," Available in PMC Apr. 13, 2015, published in final edited form as: Chem Commun (Camb). 51(26): 5747-5750 (2015) (9 pages).
Matsuzaki et al., "Dendritic spine geometry is critical for AMPA receptor expression in hippocampal CA1 pyramidal neurons," Nat Neurosci. 4(11): 1086-92 (2001).
Mizuta et al., "Design, synthesis, photochemical properties and cytotoxic activities of water-soluble caged L-leucyl-L-leucine methyl esters that control apoptosis of immune cells," Bioorg Med Chem. 10(3): 675-83 (2002).
Pinheiro et al., "Challenges and opportunities for structural DNA nanotechnology," Nat Nanotechnol. 6(12): 763-72 (2011).
Watanabe et al., "Caged compounds with a steroid skeleton: synthesis, liposome-formation and photolysis," Tetrahedron. 58(9): 1685-91 (2002).
Wegner et al., "Photocleavable linker for the patterning of bioactive molecules," Sci Rep. 5, Article No. 18309 (2015) (7 pages).

* cited by examiner

*Primary Examiner* — Tracy Vivlemore
(74) *Attorney, Agent, or Firm* — Clark & Elbing LLP

(57) ABSTRACT

The invention provides oligonucleotide conjugates including a photolabile crosslinker attached to a cargo moiety, e.g., a therapeutic or diagnostic agent. The invention further provides reagents useful in the preparation of such conjugates and methods of their use.

24 Claims, 10 Drawing Sheets
Specification includes a Sequence Listing.

FIGS. 2A-2C
Fig. 2A
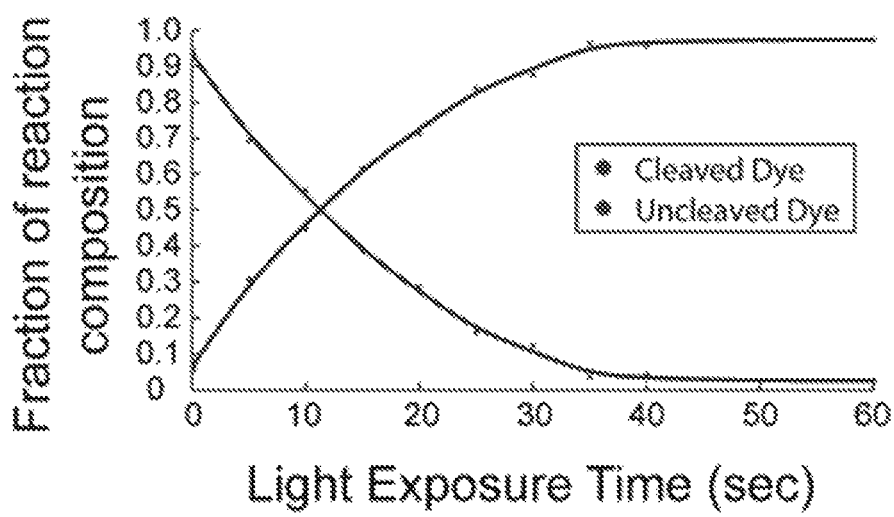
Fig. 2B
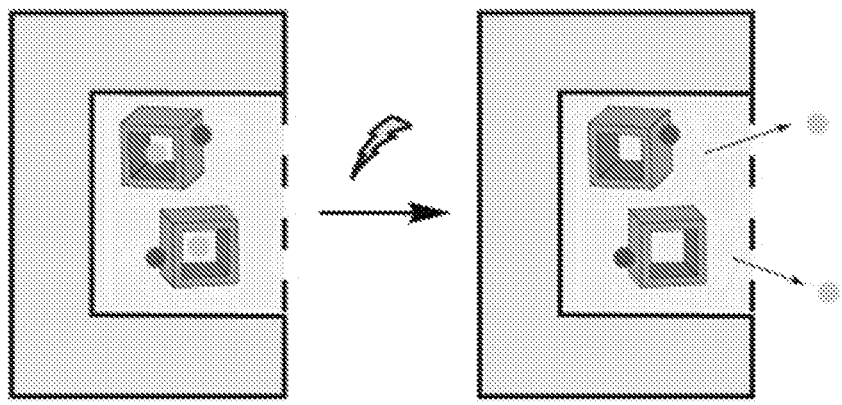
Fig. 2C
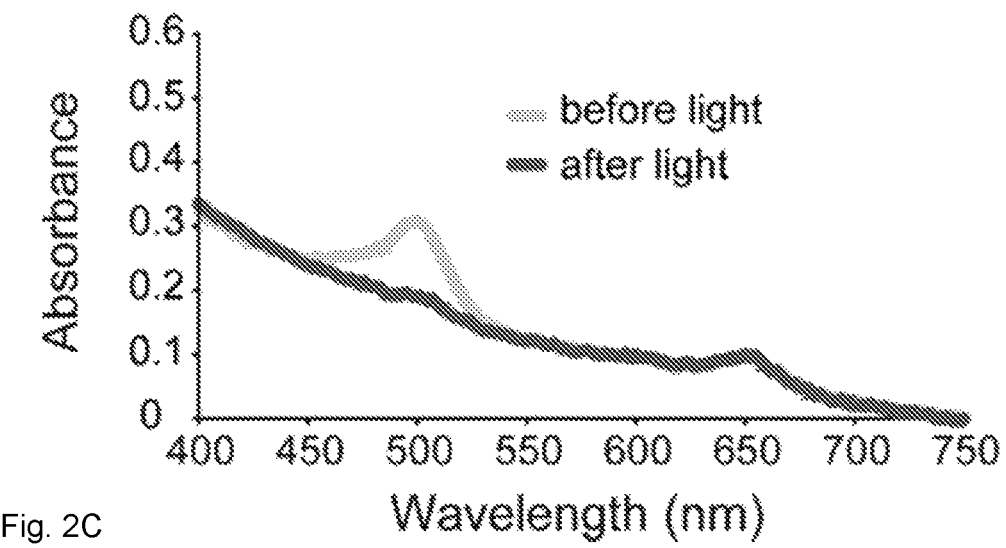

FIGS. 3A-3B
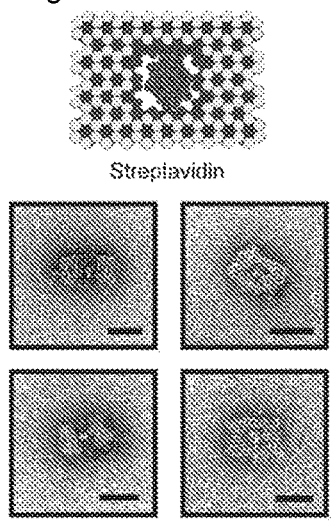
Fig. 3Ai
Streptavidin
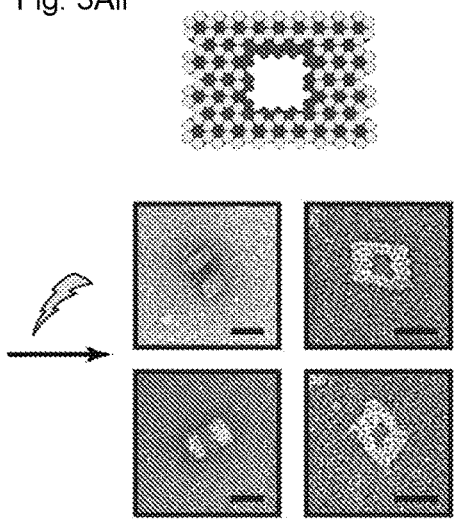
Fig. 3Aii
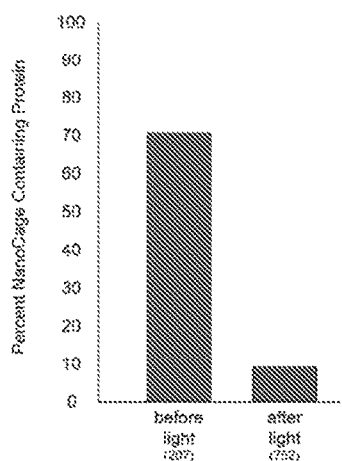
Fig. 3Aiii
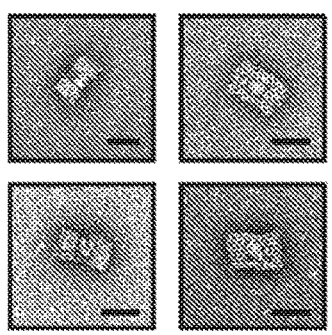
Fig. 3Bi
Bovine Serum Albumin
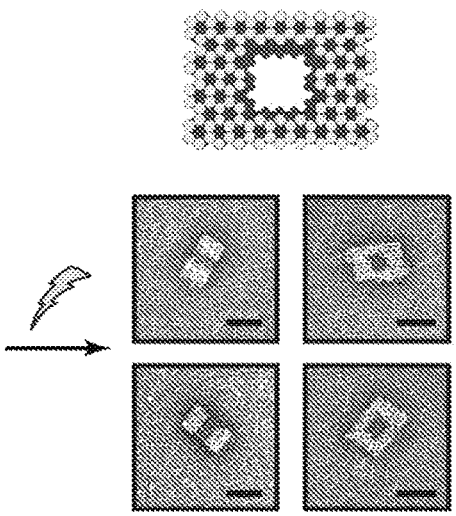
Fig. 3Bii
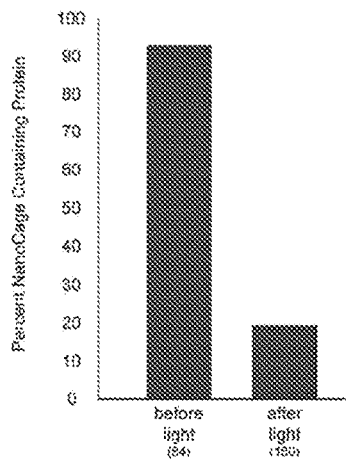
Fig. 3Biii FIGS. 4A-4D
Fig. 4A
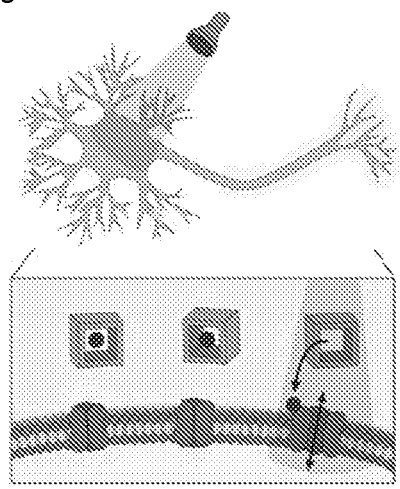
Fig. 4B
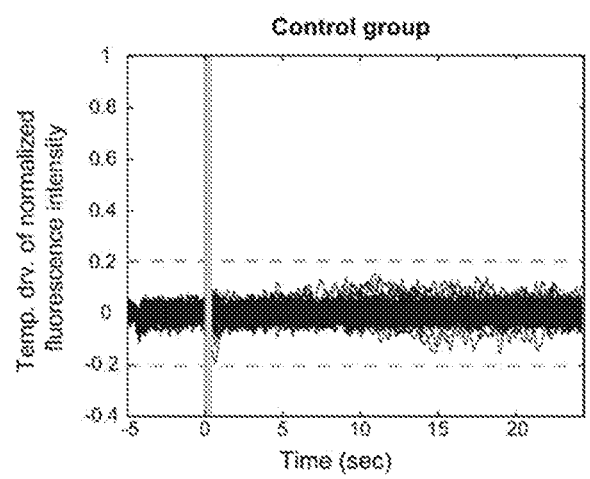
Fig. 4C
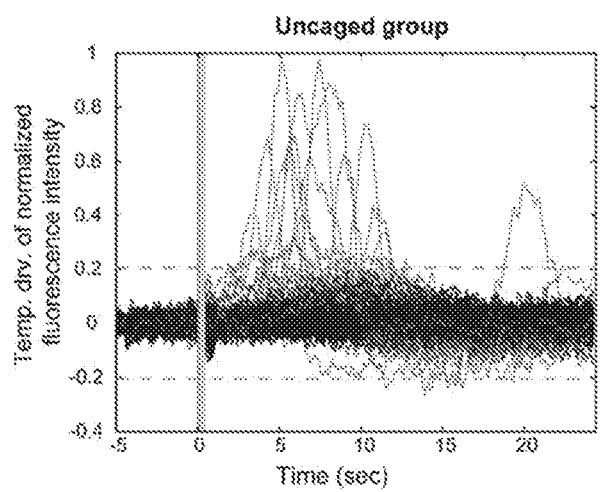
Fig. 4D
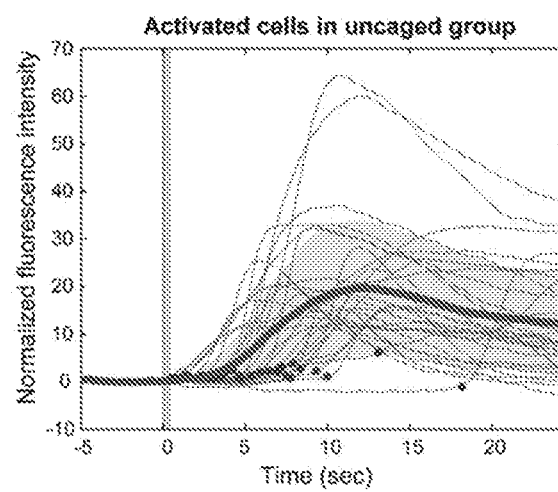

Before Light

After Light

Before Light

After Light

FIGS. 10A-10B
Fig. 10A
Glutamate-linker-oligonucleotide
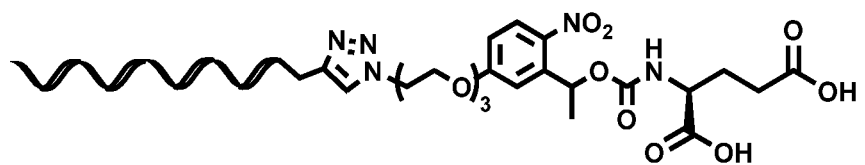
Fig. 10B
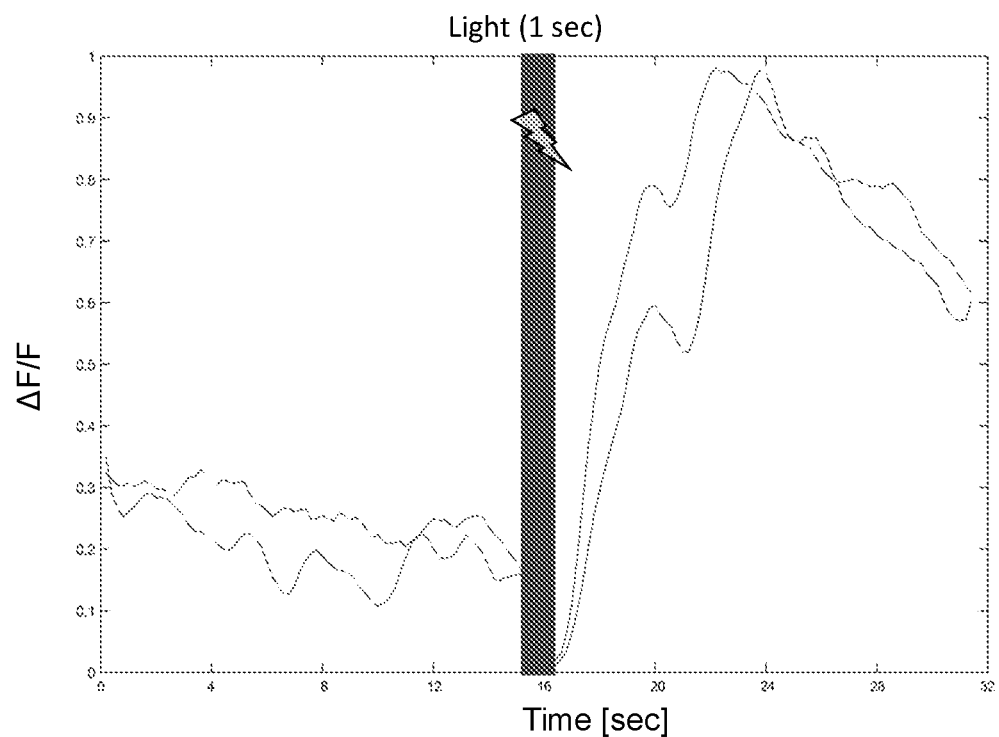

```
SEQUENCE LISTING

<160> NUMBER OF SEQ ID NOS: 217

<210> SEQ ID NO 1
<211> LENGTH: 21
<212> TYPE: DNA
<213> ORGANISM: Artificial Sequence
<220> FEATURE:
<223> OTHER INFORMATION: synthetic construct

<400> SEQUENCE: 1
ggattagcaa tataaaaagc g                                                   21

<210> SEQ ID NO 2
<211> LENGTH: 25
<212> TYPE: DNA
<213> ORGANISM: Artificial Sequence
<220> FEATURE:
<223> OTHER INFORMATION: synthetic construct

<400> SEQUENCE: 2
aatcgtcata aatattcaga atttg                                               25

<210> SEQ ID NO 3
<211> LENGTH: 25
<212> TYPE: DNA
<213> ORGANISM: Artificial Sequence
<220> FEATURE:
<223> OTHER INFORMATION: synthetic construct

<400> SEQUENCE: 3
caatagaaag ggcgacatta actgt                                               25

<210> SEQ ID NO 4
<211> LENGTH: 25
<212> TYPE: DNA
<213> ORGANISM: Artificial Sequence
<220> FEATURE:
<223> OTHER INFORMATION: synthetic construct

<400> SEQUENCE: 4
cgaaagaagg ctttgaggag cacag                                               25
```

<210> SEQ ID NO 5
<211> LENGTH: 25
<212> TYPE: DNA
<213> ORGANISM: Artificial Sequence
<220> FEATURE:
<223> OTHER INFORMATION: synthetic construct

<400> SEQUENCE: 5
gcccgaaatt gcattggaag tgcga          25

<210> SEQ ID NO 6
<211> LENGTH: 25
<212> TYPE: DNA
<213> ORGANISM: Artificial Sequence
<220> FEATURE:
<223> OTHER INFORMATION: synthetic construct

<400> SEQUENCE: 6 tacctttta cattacaaac atacc          25

<210> SEQ ID NO 7
<211> LENGTH: 28
<212> TYPE: DNA
<213> ORGANISM: Artificial Sequence
<220> FEATURE:
<223> OTHER INFORMATION: synthetic construct

<400> SEQUENCE: 7
attatcagga attatcatcg ttgcctta          28

<210> SEQ ID NO 8
<211> LENGTH: 28
<212> TYPE: DNA
<213> ORGANISM: Artificial Sequence
<220> FEATURE:
<223> OTHER INFORMATION: synthetic construct

<400> SEQUENCE: 8
cagacgagca ttgaagaacc aatgaaac          28

<210> SEQ ID NO 9
<211> LENGTH: 28
<212> TYPE: DNA
<213> ORGANISM: Artificial Sequence
<220> FEATURE:
<223> OTHER INFORMATION: synthetic construct

<400> SEQUENCE: 9 gaaaagaaa tccaatcgca gccaggtt          28

<210> SEQ ID NO 10
<211> LENGTH: 28
<212> TYPE: DNA
<213> ORGANISM: Artificial Sequence
<220> FEATURE:
<223> OTHER INFORMATION: synthetic construct

<400> SEQUENCE: 10
gcatgatcaa gaaaattgag taaaatag          28

<210> SEQ ID NO 11
<211> LENGTH: 28
<212> TYPE: DNA
<213> ORGANISM: Artificial Sequence
<220> FEATURE:
<223> OTHER INFORMATION: synthetic construct

<400> SEQUENCE: 11
gctataatgc agtacggatt tgggcaat                                          28

<210> SEQ ID NO 12
<211> LENGTH: 28
<212> TYPE: DNA
<213> ORGANISM: Artificial Sequence
<220> FEATURE:
<223> OTHER INFORMATION: synthetic construct

<400> SEQUENCE: 12
gggttatacc taccatatca gaagtttg                                          28

<210> SEQ ID NO 13
<211> LENGTH: 28
<212> TYPE: DNA
<213> ORGANISM: Artificial Sequence
<220> FEATURE:
<223> OTHER INFORMATION: synthetic construct

<400> SEQUENCE: 13
tccgcgacat cgccaccttga taggacgt                                         28

<210> SEQ ID NO 14
<211> LENGTH: 28
<212> TYPE: DNA
<213> ORGANISM: Artificial Sequence
<220> FEATURE:
<223> OTHER INFORMATION: synthetic construct

<400> SEQUENCE: 14
tttgtcaggc aacaacgtag agcaactg                                          28

<210> SEQ ID NO 15
<211> LENGTH: 31
<212> TYPE: DNA
<213> ORGANISM: Artificial Sequence
<220> FEATURE:
<223> OTHER INFORMATION: synthetic construct

<400> SEQUENCE: 15
atacgtttta gcgaaccgaa cgcctacgca t                                      31

<210> SEQ ID NO 16
<211> LENGTH: 35
<212> TYPE: DNA
<213> ORGANISM: Artificial Sequence
<220> FEATURE:
<223> OTHER INFORMATION: synthetic construct

<400> SEQUENCE: 16
tttccttgaa aacagtcaat agtgaagagt gtaac                                  35

<210> SEQ ID NO 17
<211> LENGTH: 38
<212> TYPE: DNA
<213> ORGANISM: Artificial Sequence
<220> FEATURE:
<223> OTHER INFORMATION: synthetic construct

<400> SEQUENCE: 17
taaatcatcc agtttggaag cgccagggag ctgattat                               38

<210> SEQ ID NO 18
<211> LENGTH: 39

<212> TYPE: DNA
<213> ORGANISM: Artificial Sequence
<220> FEATURE:
<223> OTHER INFORMATION: synthetic construct

<400> SEQUENCE: 18
ccctcaagac ggaataggtg taaaagaagg caccagtaa                                39

<210> SEQ ID NO 19
<211> LENGTH: 39
<212> TYPE: DNA
<213> ORGANISM: Artificial Sequence
<220> FEATURE:
<223> OTHER INFORMATION: synthetic construct

<400> SEQUENCE: 19
gattatacat taaaaataca acgaaccgtc tatcaatca                                39

<210> SEQ ID NO 20
<211> LENGTH: 42
<212> TYPE: DNA
<213> ORGANISM: Artificial Sequence
<220> FEATURE:
<223> OTHER INFORMATION: synthetic construct

<400> SEQUENCE: 20
aaaagcggtt accagaagga aagcagatac cgaagttatc cc                            42

<210> SEQ ID NO 21
<211> LENGTH: 42
<212> TYPE: DNA
<213> ORGANISM: Artificial Sequence
<220> FEATURE:
<223> OTHER INFORMATION: synthetic construct

<400> SEQUENCE: 21
aagtttacca gacgcaaaag aagtttgtgc agacggtcga aa                            42

<210> SEQ ID NO 22
<211> LENGTH: 42
<212> TYPE: DNA
<213> ORGANISM: Artificial Sequence
<220> FEATURE:
<223> OTHER INFORMATION: synthetic construct

<400> SEQUENCE: 22
aattgggctt agaaacatca gtgaaaatca agacaagaca at                            42

<210> SEQ ID NO 23
<211> LENGTH: 42
<212> TYPE: DNA
<213> ORGANISM: Artificial Sequence
<220> FEATURE:
<223> OTHER INFORMATION: synthetic construct

<400> SEQUENCE: 23
acaaatgaat aacagctgct tgctaccagt cgcgatttct tt                            42

<210> SEQ ID NO 24
<211> LENGTH: 42
<212> TYPE: DNA
<213> ORGANISM: Artificial Sequence
<220> FEATURE:
<223> OTHER INFORMATION: synthetic construct

<400> SEQUENCE: 24
actaaggaat aactaatgtt gagaaatata tatacattaa ta                               42

<210> SEQ ID NO 25
<211> LENGTH: 42
<212> TYPE: DNA
<213> ORGANISM: Artificial Sequence
<220> FEATURE:
<223> OTHER INFORMATION: synthetic construct

<400> SEQUENCE: 25
atgaaaataa ggtaacccac aagacaatga aatagctgaa tt                               42

<210> SEQ ID NO 26
<211> LENGTH: 42
<212> TYPE: DNA
<213> ORGANISM: Artificial Sequence
<220> FEATURE:
<223> OTHER INFORMATION: synthetic construct

<400> SEQUENCE: 26
catcgtatag caccattacc aagccagccc gacttaatac cc                               42

<210> SEQ ID NO 27
<211> LENGTH: 42
<212> TYPE: DNA
<213> ORGANISM: Artificial Sequence
<220> FEATURE:
<223> OTHER INFORMATION: synthetic construct

<400> SEQUENCE: 27
ccagctacaa gtctttccat aatgggatag gtgcatctgc ac                               42

<210> SEQ ID NO 28
<211> LENGTH: 42
<212> TYPE: DNA
<213> ORGANISM: Artificial Sequence
<220> FEATURE:
<223> OTHER INFORMATION: synthetic construct

<400> SEQUENCE: 28
ctgtttactc aacagtaggg caacagtata aagccgaaaa ct                               42

<210> SEQ ID NO 29
<211> LENGTH: 42
<212> TYPE: DNA
<213> ORGANISM: Artificial Sequence
<220> FEATURE:
<223> OTHER INFORMATION: synthetic construct

<400> SEQUENCE: 29
gatgccagag ggggaatact gcggaagcac ggtgtatcat aa                               42

<210> SEQ ID NO 30
<211> LENGTH: 42
<212> TYPE: DNA
<213> ORGANISM: Artificial Sequence
<220> FEATURE:
<223> OTHER INFORMATION: synthetic construct

<400> SEQUENCE: 30
gcaaatcaca tcattaccgc gcaatagata agtcccacgc gc                               42

<210> SEQ ID NO 31
<211> LENGTH: 42
<212> TYPE: DNA
<213> ORGANISM: Artificial Sequence
<220> FEATURE:
<223> OTHER INFORMATION: synthetic construct

<400> SEQUENCE: 31
gcgcgaaatt tgaccccag caaaaaggct ccaaaaggtt ga        42

<210> SEQ ID NO 32
<211> LENGTH: 42
<212> TYPE: DNA
<213> ORGANISM: Artificial Sequence
<220> FEATURE:
<223> OTHER INFORMATION: synthetic construct

<400> SEQUENCE: 32
ggcttaaaat ttatcaaaat cataatcctg attccagata tt        42

<210> SEQ ID NO 33
<211> LENGTH: 42
<212> TYPE: DNA
<213> ORGANISM: Artificial Sequence
<220> FEATURE:
<223> OTHER INFORMATION: synthetic construct

<400> SEQUENCE: 33
tgggataaaa cactcatctc atgataccga tagcataatt tt        42

<210> SEQ ID NO 34
<211> LENGTH: 42
<212> TYPE: DNA
<213> ORGANISM: Artificial Sequence
<220> FEATURE:
<223> OTHER INFORMATION: synthetic construct

<400> SEQUENCE: 34
tttaatcata accgaccggt aaagggcatt taaaccaaat ca        42

<210> SEQ ID NO 35
<211> LENGTH: 42
<212> TYPE: DNA
<213> ORGANISM: Artificial Sequence
<220> FEATURE:
<223> OTHER INFORMATION: synthetic construct

<400> SEQUENCE: 35
ttttcaaaca agacaaagaa caaaacagaa ataaaagaaa at        42

<210> SEQ ID NO 36
<211> LENGTH: 43
<212> TYPE: DNA
<213> ORGANISM: Artificial Sequence
<220> FEATURE:
<223> OTHER INFORMATION: synthetic construct

<400> SEQUENCE: 36
atacgagccg ggagtgagag gtgagcacgc tggaaattgt aca        43

<210> SEQ ID NO 37
<211> LENGTH: 45
<212> TYPE: DNA
<213> ORGANISM: Artificial Sequence
<220> FEATURE:
<223> OTHER INFORMATION: synthetic construct

<400> SEQUENCE: 37
aattcatgag tacaaacgcc tggcgggcaa ctggttttgc ggttt        45

<210> SEQ ID NO 38
<211> LENGTH: 45
<212> TYPE: DNA
<213> ORGANISM: Artificial Sequence
<220> FEATURE:
<223> OTHER INFORMATION: synthetic construct

<400> SEQUENCE: 38
atatcaatca aaaacattc gcgtccaata gagctttcat agcaa        45

<210> SEQ ID NO 39
<211> LENGTH: 45
<212> TYPE: DNA
<213> ORGANISM: Artificial Sequence
<220> FEATURE:
<223> OTHER INFORMATION: synthetic construct

<400> SEQUENCE: 39
ccaccaccac cggaatccaa aaagggtctt taccctgatc cataa        45

<210> SEQ ID NO 40
<211> LENGTH: 45
<212> TYPE: DNA
<213> ORGANISM: Artificial Sequence
<220> FEATURE:
<223> OTHER INFORMATION: synthetic construct

<400> SEQUENCE: 40
gaatacacta acgccaaatc ataaccctct ttgataaaat accaa        45

<210> SEQ ID NO 41
<211> LENGTH: 45
<212> TYPE: DNA
<213> ORGANISM: Artificial Sequence
<220> FEATURE:
<223> OTHER INFORMATION: synthetic construct

<400> SEQUENCE: 41
tatttgcaga agataaaaca gctcgaacga accacttgca tgccc        45

<210> SEQ ID NO 42
<211> LENGTH: 45
<212> TYPE: DNA
<213> ORGANISM: Artificial Sequence
<220> FEATURE:
<223> OTHER INFORMATION: synthetic construct

<400> SEQUENCE: 42
ttctgccgcc tccctcagcc accaccctca ttcaaagcag aggaa        45

<210> SEQ ID NO 43
<211> LENGTH: 46
<212> TYPE: DNA
<213> ORGANISM: Artificial Sequence
<220> FEATURE:
<223> OTHER INFORMATION: synthetic construct

<400> SEQUENCE: 43
aaatctcgcg taacgatcta aagacagctg agtttcgtca ccctaa        46

<210> SEQ ID NO 44
<211> LENGTH: 46
<212> TYPE: DNA
<213> ORGANISM: Artificial Sequence
<220> FEATURE:
<223> OTHER INFORMATION: synthetic construct

<400> SEQUENCE: 44
accgtcaaaa atcaccaagc aataaagcaa acatttagct atgctg            46

<210> SEQ ID NO 45
<211> LENGTH: 46
<212> TYPE: DNA
<213> ORGANISM: Artificial Sequence
<220> FEATURE:
<223> OTHER INFORMATION: synthetic construct

<400> SEQUENCE: 45
cgccacccag gaggttgctc cttttgataa ttgctcatcc aaattc            46

<210> SEQ ID NO 46
<211> LENGTH: 46
<212> TYPE: DNA
<213> ORGANISM: Artificial Sequence
<220> FEATURE:
<223> OTHER INFORMATION: synthetic construct

<400> SEQUENCE: 46
ctatcttagc cgaacatgag agtctggaaa actagcaacc cgatca            46

<210> SEQ ID NO 47
<211> LENGTH: 46
<212> TYPE: DNA
<213> ORGANISM: Artificial Sequence
<220> FEATURE:
<223> OTHER INFORMATION: synthetic construct

<400> SEQUENCE: 47
tgtttccaac ctgtctcaca taatatcacc agcagttgaa tatacc            46

<210> SEQ ID NO 48
<211> LENGTH: 49
<212> TYPE: DNA
<213> ORGANISM: Artificial Sequence
<220> FEATURE:
<223> OTHER INFORMATION: synthetic construct

<400> SEQUENCE: 48
aataaataca aacaaccgat tgagattaaa ggtgaagata atagttatt         49

<210> SEQ ID NO 49
<211> LENGTH: 49
<212> TYPE: DNA
<213> ORGANISM: Artificial Sequence
<220> FEATURE:
<223> OTHER INFORMATION: synthetic construct

<400> SEQUENCE: 49
acagtttgag gcactccagc ctcccgactt gttgctattt tgccattaa         49

<210> SEQ ID NO 50
<211> LENGTH: 49
<212> TYPE: DNA
<213> ORGANISM: Artificial Sequence
<220> FEATURE:
<223> OTHER INFORMATION: synthetic construct

<400> SEQUENCE: 50
agagagccgc ttgcctttag cgtaagatag cagcaccgat tattcggag         49

<210> SEQ ID NO 51

<211> LENGTH: 49
<212> TYPE: DNA
<213> ORGANISM: Artificial Sequence
<220> FEATURE:
<223> OTHER INFORMATION: synthetic construct

<400> SEQUENCE: 51
ccgacaatat tcggtattaa aatcggcaaa atccccccag catcagcag           49

<210> SEQ ID NO 52
<211> LENGTH: 49
<212> TYPE: DNA
<213> ORGANISM: Artificial Sequence
<220> FEATURE:
<223> OTHER INFORMATION: synthetic construct

<400> SEQUENCE: 52
gtaatatatt tggtttgtta attgatttag gtgaacaatg tagaaagat           49

<210> SEQ ID NO 53
<211> LENGTH: 49
<212> TYPE: DNA
<213> ORGANISM: Artificial Sequence
<220> FEATURE:
<223> OTHER INFORMATION: synthetic construct

<400> SEQUENCE: 53
ttggtgagaa gctacagcag catcccacgc tggtttgcct tcaccaatt           49

<210> SEQ ID NO 54
<211> LENGTH: 56
<212> TYPE: DNA
<213> ORGANISM: Artificial Sequence
<220> FEATURE:
<223> OTHER INFORMATION: synthetic construct

<400> SEQUENCE: 54
caagaaaaat ctactacagg tttgcttctt aaaagtttga cacaactcgt cctaaa    56

<210> SEQ ID NO 55
<211> LENGTH: 21
<212> TYPE: DNA
<213> ORGANISM: Artificial Sequence
<220> FEATURE:
<223> OTHER INFORMATION: synthetic construct

<400> SEQUENCE: 55
ttgactacct ttttaacctc c                                         21

<210> SEQ ID NO 56
<211> LENGTH: 22
<212> TYPE: DNA
<213> ORGANISM: Artificial Sequence
<220> FEATURE:
<223> OTHER INFORMATION: synthetic construct

<400> SEQUENCE: 56
ttatgaacgg tcccggttga tt                                        22

<210> SEQ ID NO 57
<211> LENGTH: 22
<212> TYPE: DNA
<213> ORGANISM: Artificial Sequence
<220> FEATURE:
<223> OTHER INFORMATION: synthetic construct

<400> SEQUENCE: 57
tttcattacc cataaggctt tt                                           22

<210> SEQ ID NO 58
<211> LENGTH: 22
<212> TYPE: DNA
<213> ORGANISM: Artificial Sequence
<220> FEATURE:
<223> OTHER INFORMATION: synthetic construct

<400> SEQUENCE: 58
ttaaccacca gagcccgaga tt                                           22

<210> SEQ ID NO 59
<211> LENGTH: 22
<212> TYPE: DNA
<213> ORGANISM: Artificial Sequence
<220> FEATURE:
<223> OTHER INFORMATION: synthetic construct

<400> SEQUENCE: 59
ttgggcgcat ccgacagtat tt                                           22

<210> SEQ ID NO 60
<211> LENGTH: 22
<212> TYPE: DNA
<213> ORGANISM: Artificial Sequence
<220> FEATURE:
<223> OTHER INFORMATION: synthetic construct

<400> SEQUENCE: 60
ttccacgcat aagttaaagg tt                                           22

<210> SEQ ID NO 61
<211> LENGTH: 22
<212> TYPE: DNA
<213> ORGANISM: Artificial Sequence
<220> FEATURE:
<223> OTHER INFORMATION: synthetic construct

<400> SEQUENCE: 61
ttgctcatta tttcgaggtg tt                                           22

<210> SEQ ID NO 62
<211> LENGTH: 22
<212> TYPE: DNA
<213> ORGANISM: Artificial Sequence
<220> FEATURE:
<223> OTHER INFORMATION: synthetic construct

<400> SEQUENCE: 62
ttttaaatat gcatataaca tt                                           22

<210> SEQ ID NO 63
<211> LENGTH: 22
<212> TYPE: DNA
<213> ORGANISM: Artificial Sequence
<220> FEATURE:
<223> OTHER INFORMATION: synthetic construct

<400> SEQUENCE: 63
ttcggcctca ggcttctggt tt                                           22

<210> SEQ ID NO 64
<211> LENGTH: 22
<212> TYPE: DNA

```
<213> ORGANISM: Artificial Sequence
<220> FEATURE:
<223> OTHER INFORMATION: synthetic construct

<400> SEQUENCE: 64
tttaatcaga aatatttaaa tt                                          22

<210> SEQ ID NO 65
<211> LENGTH: 22
<212> TYPE: DNA
<213> ORGANISM: Artificial Sequence
<220> FEATURE:
<223> OTHER INFORMATION: synthetic construct

<400> SEQUENCE: 65
ttaatttctt atttctgtat tt                                          22

<210> SEQ ID NO 66
<211> LENGTH: 22
<212> TYPE: DNA
<213> ORGANISM: Artificial Sequence
<220> FEATURE:
<223> OTHER INFORMATION: synthetic construct

<400> SEQUENCE: 66
tttaatttca ataagaactg tt                                          22

<210> SEQ ID NO 67
<211> LENGTH: 22
<212> TYPE: DNA
<213> ORGANISM: Artificial Sequence
<220> FEATURE:
<223> OTHER INFORMATION: synthetic construct

<400> SEQUENCE: 67
ttaaatcggt ttgcgggaga tt                                          22

<210> SEQ ID NO 68
<211> LENGTH: 22
<212> TYPE: DNA
<213> ORGANISM: Artificial Sequence
<220> FEATURE:
<223> OTHER INFORMATION: synthetic construct

<400> SEQUENCE: 68
tttaagacgc tgaacaaaga tt                                          22

<210> SEQ ID NO 69
<211> LENGTH: 22
<212> TYPE: DNA
<213> ORGANISM: Artificial Sequence
<220> FEATURE:
<223> OTHER INFORMATION: synthetic construct

<400> SEQUENCE: 69
ttgccctgac ggagatggtt tt                                          22

<210> SEQ ID NO 70
<211> LENGTH: 22
<212> TYPE: DNA
<213> ORGANISM: Artificial Sequence
<220> FEATURE:
<223> OTHER INFORMATION: synthetic construct

<400> SEQUENCE: 70
ttaacggaac aaaccatcgc tt                                          22
```

```
<210> SEQ ID NO 71
<211> LENGTH: 22
<212> TYPE: DNA
<213> ORGANISM: Artificial Sequence
<220> FEATURE:
<223> OTHER INFORMATION: synthetic construct

<400> SEQUENCE: 71
ttgttgattc caccggatat tt                                              22

<210> SEQ ID NO 72
<211> LENGTH: 22
<212> TYPE: DNA
<213> ORGANISM: Artificial Sequence
<220> FEATURE:
<223> OTHER INFORMATION: synthetic construct

<400> SEQUENCE: 72 ttagcccttta tcatatattt tt                                             22

<210> SEQ ID NO 73
<211> LENGTH: 22
<212> TYPE: DNA
<213> ORGANISM: Artificial Sequence
<220> FEATURE:
<223> OTHER INFORMATION: synthetic construct

<400> SEQUENCE: 73
ttggatggct tcaacatgtt tt                                              22

<210> SEQ ID NO 74
<211> LENGTH: 25
<212> TYPE: DNA
<213> ORGANISM: Artificial Sequence
<220> FEATURE:
<223> OTHER INFORMATION: synthetic construct

<400> SEQUENCE: 74
ttacggccag taggatcccc gggtt                                           25

<210> SEQ ID NO 75
<211> LENGTH: 25
<212> TYPE: DNA
<213> ORGANISM: Artificial Sequence
<220> FEATURE:
<223> OTHER INFORMATION: synthetic construct

<400> SEQUENCE: 75
ttgggatttt gagtacaaac tactt                                           25

<210> SEQ ID NO 76
<211> LENGTH: 28
<212> TYPE: DNA
<213> ORGANISM: Artificial Sequence
<220> FEATURE:
<223> OTHER INFORMATION: synthetic construct

<400> SEQUENCE: 76
tttgtaccaa ctcagagcat aaagcttt                                        28

<210> SEQ ID NO 77
<211> LENGTH: 28
<212> TYPE: DNA
<213> ORGANISM: Artificial Sequence
<220> FEATURE:
```

<223> OTHER INFORMATION: synthetic construct

<400> SEQUENCE: 77
cgagtaaccg tcacgttggt gtagattt                28

<210> SEQ ID NO 78
<211> LENGTH: 28
<212> TYPE: DNA
<213> ORGANISM: Artificial Sequence
<220> FEATURE:
<223> OTHER INFORMATION: synthetic construct

<400> SEQUENCE: 78
aacacattat gttaataaaa cgaacttt                28

<210> SEQ ID NO 79
<211> LENGTH: 28
<212> TYPE: DNA
<213> ORGANISM: Artificial Sequence
<220> FEATURE:
<223> OTHER INFORMATION: synthetic construct

<400> SEQUENCE: 79
tacaatcgta gcaaacaaga gaatcgtt                28

<210> SEQ ID NO 80
<211> LENGTH: 28
<212> TYPE: DNA
<213> ORGANISM: Artificial Sequence
<220> FEATURE:
<223> OTHER INFORMATION: synthetic construct

<400> SEQUENCE: 80
ttacaacatg ttcagagaac aagcaatt                28

<210> SEQ ID NO 81
<211> LENGTH: 28
<212> TYPE: DNA
<213> ORGANISM: Artificial Sequence
<220> FEATURE:
<223> OTHER INFORMATION: synthetic construct

<400> SEQUENCE: 81
ttgaagcaaa gcggagactt caaatatt                28

<210> SEQ ID NO 82
<211> LENGTH: 28
<212> TYPE: DNA
<213> ORGANISM: Artificial Sequence
<220> FEATURE:
<223> OTHER INFORMATION: synthetic construct

<400> SEQUENCE: 82
ttttgtatcg gtttacaaag tacaactt                28

<210> SEQ ID NO 83
<211> LENGTH: 28
<212> TYPE: DNA
<213> ORGANISM: Artificial Sequence
<220> FEATURE:
<223> OTHER INFORMATION: synthetic construct

<400> SEQUENCE: 83
tttttgaaag aggactggct gacctttt                28

<210> SEQ ID NO 84
<211> LENGTH: 28
<212> TYPE: DNA
<213> ORGANISM: Artificial Sequence
<220> FEATURE:
<223> OTHER INFORMATION: synthetic construct

<400> SEQUENCE: 84
ttggactcca acgtatcaga tgatggtt                                             28

<210> SEQ ID NO 85
<211> LENGTH: 28
<212> TYPE: DNA
<213> ORGANISM: Artificial Sequence
<220> FEATURE:
<223> OTHER INFORMATION: synthetic construct

<400> SEQUENCE: 85
ttgccgtttt tattttgtta aatcagtt                                             28

<210> SEQ ID NO 86
<211> LENGTH: 29
<212> TYPE: DNA
<213> ORGANISM: Artificial Sequence
<220> FEATURE:
<223> OTHER INFORMATION: synthetic construct

<400> SEQUENCE: 86
tttagggttg agtgttgtaa agaataagg                                            29

<210> SEQ ID NO 87
<211> LENGTH: 28
<212> TYPE: DNA
<213> ORGANISM: Artificial Sequence
<220> FEATURE:
<223> OTHER INFORMATION: synthetic construct

<400> SEQUENCE: 87
tttcaaccgt tctattttga gagatctt                                             28

<210> SEQ ID NO 88
<211> LENGTH: 28
<212> TYPE: DNA
<213> ORGANISM: Artificial Sequence
<220> FEATURE:
<223> OTHER INFORMATION: synthetic construct

<400> SEQUENCE: 88
ttctaaaaca tcgccttctg aataattt                                             28

<210> SEQ ID NO 89
<211> LENGTH: 28
<212> TYPE: DNA
<213> ORGANISM: Artificial Sequence
<220> FEATURE:
<223> OTHER INFORMATION: synthetic construct

<400> SEQUENCE: 89
tttttccaga cgttaggagc ctttaatt                                             28

<210> SEQ ID NO 90
<211> LENGTH: 28
<212> TYPE: DNA
<213> ORGANISM: Artificial Sequence
<220> FEATURE:
<223> OTHER INFORMATION: synthetic construct

<400> SEQUENCE: 90
ttggagattt gtatcctgct ccatgttt                                28

<210> SEQ ID NO 91
<211> LENGTH: 28
<212> TYPE: DNA
<213> ORGANISM: Artificial Sequence
<220> FEATURE:
<223> OTHER INFORMATION: synthetic construct

<400> SEQUENCE: 91
ttcatcaaga gtaactatta tagtcatt                                28

<210> SEQ ID NO 92
<211> LENGTH: 28
<212> TYPE: DNA
<213> ORGANISM: Artificial Sequence
<220> FEATURE:
<223> OTHER INFORMATION: synthetic construct

<400> SEQUENCE: 92
ttaaatgctg atgccctgtt tagtattt                                28

<210> SEQ ID NO 93
<211> LENGTH: 28
<212> TYPE: DNA
<213> ORGANISM: Artificial Sequence
<220> FEATURE:
<223> OTHER INFORMATION: synthetic construct

<400> SEQUENCE: 93
tttacttagc cggagaactg accaactt                                28

<210> SEQ ID NO 94
<211> LENGTH: 28
<212> TYPE: DNA
<213> ORGANISM: Artificial Sequence
<220> FEATURE:
<223> OTHER INFORMATION: synthetic construct

<400> SEQUENCE: 94
ttttcgcaaa tggtgcgcga gctgaatt                                28

<210> SEQ ID NO 95
<211> LENGTH: 28
<212> TYPE: DNA
<213> ORGANISM: Artificial Sequence
<220> FEATURE:
<223> OTHER INFORMATION: synthetic construct

<400> SEQUENCE: 95
ttaaggtggc atcataaatc atacagtt                                28

<210> SEQ ID NO 96
<211> LENGTH: 28
<212> TYPE: DNA
<213> ORGANISM: Artificial Sequence
<220> FEATURE:
<223> OTHER INFORMATION: synthetic construct

<400> SEQUENCE: 96
tttcgcgttt taatactcca acaggttt                                28

<210> SEQ ID NO 97
<211> LENGTH: 28

<212> TYPE: DNA
<213> ORGANISM: Artificial Sequence
<220> FEATURE:
<223> OTHER INFORMATION: synthetic construct

<400> SEQUENCE: 97
tttagccagc tttctcggat tctccgtt					28

<210> SEQ ID NO 98
<211> LENGTH: 28
<212> TYPE: DNA
<213> ORGANISM: Artificial Sequence
<220> FEATURE:
<223> OTHER INFORMATION: synthetic construct

<400> SEQUENCE: 98
ttcatatgcg ttatcgacga caataatt					28

<210> SEQ ID NO 99
<211> LENGTH: 28
<212> TYPE: DNA
<213> ORGANISM: Artificial Sequence
<220> FEATURE:
<223> OTHER INFORMATION: synthetic construct

<400> SEQUENCE: 99
ttcaattcat caatataggt ctgagatt					28

<210> SEQ ID NO 100
<211> LENGTH: 28
<212> TYPE: DNA
<213> ORGANISM: Artificial Sequence
<220> FEATURE:
<223> OTHER INFORMATION: synthetic construct

<400> SEQUENCE: 100
ttggaagggt tagaataact atatgttt					28

<210> SEQ ID NO 101
<211> LENGTH: 28
<212> TYPE: DNA
<213> ORGANISM: Artificial Sequence
<220> FEATURE:
<223> OTHER INFORMATION: synthetic construct

<400> SEQUENCE: 101
ttacgttatt aatttgtaaa tcgtcgtt					28

<210> SEQ ID NO 102
<211> LENGTH: 28
<212> TYPE: DNA
<213> ORGANISM: Artificial Sequence
<220> FEATURE:
<223> OTHER INFORMATION: synthetic construct

<400> SEQUENCE: 102
ttggtggttc cgaatccttt gcccgatt					28

<210> SEQ ID NO 103
<211> LENGTH: 28
<212> TYPE: DNA
<213> ORGANISM: Artificial Sequence
<220> FEATURE:
<223> OTHER INFORMATION: synthetic construct

<400> SEQUENCE: 103
ttctcatttt ttaactggcc ttcctgtt                                        28

<210> SEQ ID NO 104
<211> LENGTH: 31
<212> TYPE: DNA
<213> ORGANISM: Artificial Sequence
<220> FEATURE:
<223> OTHER INFORMATION: synthetic construct

<400> SEQUENCE: 104
ttaagattta gtttgaccat tagatacatt t                                    31

<210> SEQ ID NO 105
<211> LENGTH: 35
<212> TYPE: DNA
<213> ORGANISM: Artificial Sequence
<220> FEATURE:
<223> OTHER INFORMATION: synthetic construct

<400> SEQUENCE: 105
agcttttgcg gagaagatag cgatagctta gattt                                35

<210> SEQ ID NO 106
<211> LENGTH: 36
<212> TYPE: DNA
<213> ORGANISM: Artificial Sequence
<220> FEATURE:
<223> OTHER INFORMATION: synthetic construct

<400> SEQUENCE: 106
ttccgctttt gcgggatctg cagggaccga tatgac                               36

<210> SEQ ID NO 107
<211> LENGTH: 35
<212> TYPE: DNA
<213> ORGANISM: Artificial Sequence
<220> FEATURE:
<223> OTHER INFORMATION: synthetic construct

<400> SEQUENCE: 107
ttaacgcctg tagcattcca cagttttgtc gtctt                                35

<210> SEQ ID NO 108
<211> LENGTH: 36
<212> TYPE: DNA
<213> ORGANISM: Artificial Sequence
<220> FEATURE:
<223> OTHER INFORMATION: synthetic construct

<400> SEQUENCE: 108
ttgccggaaa ccaggccacg gcaccgaaga tcggga                               36

<210> SEQ ID NO 109
<211> LENGTH: 36
<212> TYPE: DNA
<213> ORGANISM: Artificial Sequence
<220> FEATURE:
<223> OTHER INFORMATION: synthetic construct

<400> SEQUENCE: 109
ttttgtaaac gttaatatta agcaaaagcc cctatg                               36

<210> SEQ ID NO 110
<211> LENGTH: 35
<212> TYPE: DNA
<213> ORGANISM: Artificial Sequence

```
<220> FEATURE:
<223> OTHER INFORMATION: synthetic construct

<400> SEQUENCE: 110
tttaccgagc tcgaattcgt agaactgata gcctt                              35

<210> SEQ ID NO 111
<211> LENGTH: 36
<212> TYPE: DNA
<213> ORGANISM: Artificial Sequence
<220> FEATURE:
<223> OTHER INFORMATION: synthetic construct

<400> SEQUENCE: 111
tttaaatgca atgcctgaga accctttcaa cgatac                             36

<210> SEQ ID NO 112
<211> LENGTH: 36
<212> TYPE: DNA
<213> ORGANISM: Artificial Sequence
<220> FEATURE:
<223> OTHER INFORMATION: synthetic construct

<400> SEQUENCE: 112
ttcaaggcga ttaagtgtgc aggggatgt gctgtt                              36

<210> SEQ ID NO 113
<211> LENGTH: 36
<212> TYPE: DNA
<213> ORGANISM: Artificial Sequence
<220> FEATURE:
<223> OTHER INFORMATION: synthetic construct

<400> SEQUENCE: 113
ttcattcagg ctgcgcaacc aaagcgccat tcgctt                             36

<210> SEQ ID NO 114
<211> LENGTH: 36
<212> TYPE: DNA
<213> ORGANISM: Artificial Sequence
<220> FEATURE:
<223> OTHER INFORMATION: synthetic construct

<400> SEQUENCE: 114
ttgttttccc agtcacgcac tgggtaacgc caggtt                             36

<210> SEQ ID NO 115
<211> LENGTH: 38
<212> TYPE: DNA
<213> ORGANISM: Artificial Sequence
<220> FEATURE:
<223> OTHER INFORMATION: synthetic construct

<400> SEQUENCE: 115
tacccctgta caaggattac accatcaata tgatattt                           38

<210> SEQ ID NO 116
<211> LENGTH: 36
<212> TYPE: DNA
<213> ORGANISM: Artificial Sequence
<220> FEATURE:
<223> OTHER INFORMATION: synthetic construct

<400> SEQUENCE: 116
ttcgccagct ggcgaagaaa cctcttcgct attatt                             36
```

<210> SEQ ID NO 117
<211> LENGTH: 36
<212> TYPE: DNA
<213> ORGANISM: Artificial Sequence
<220> FEATURE:
<223> OTHER INFORMATION: synthetic construct

<400> SEQUENCE: 117
ttgcgatcgg tgcgggcgtc aactgttggg aaggtt                        36

<210> SEQ ID NO 118
<211> LENGTH: 42
<212> TYPE: DNA
<213> ORGANISM: Artificial Sequence
<220> FEATURE:
<223> OTHER INFORMATION: synthetic construct

<400> SEQUENCE: 118
tggcaggtcg actctaggcc aagccagacg ttgtaaaacg tt                 42

<210> SEQ ID NO 119
<211> LENGTH: 42
<212> TYPE: DNA
<213> ORGANISM: Artificial Sequence
<220> FEATURE:
<223> OTHER INFORMATION: synthetic construct

<400> SEQUENCE: 119
tttgggaaca aacggcggat tgaccggacg agtaacaaat ag                 42

<210> SEQ ID NO 120
<211> LENGTH: 42
<212> TYPE: DNA
<213> ORGANISM: Artificial Sequence
<220> FEATURE:
<223> OTHER INFORMATION: synthetic construct

<400> SEQUENCE: 120
tttacaaagg ctatcaggtc attgccaaga gagggattta tc                 42

<210> SEQ ID NO 121
<211> LENGTH: 42
<212> TYPE: DNA
<213> ORGANISM: Artificial Sequence
<220> FEATURE:
<223> OTHER INFORMATION: synthetic construct

<400> SEQUENCE: 121
ttgcaaggca aagaattagc aaaattaggc attaagaaga gc                 42

<210> SEQ ID NO 122
<211> LENGTH: 46
<212> TYPE: DNA
<213> ORGANISM: Artificial Sequence
<220> FEATURE:
<223> OTHER INFORMATION: synthetic construct

<400> SEQUENCE: 122
ttcaggatta gagagtacct ttaattgaca gaccggaagc aatcga             46

<210> SEQ ID NO 123
<211> LENGTH: 49
<212> TYPE: DNA
<213> ORGANISM: Artificial Sequence
<220> FEATURE:
<223> OTHER INFORMATION: synthetic construct

```
<400> SEQUENCE: 123
ttcactaact ttcatgaggc tgtcacccgg cgaaaatcct gtttgattt          49

<210> SEQ ID NO 124
<211> LENGTH: 49
<212> TYPE: DNA
<213> ORGANISM: Artificial Sequence
<220> FEATURE:
<223> OTHER INFORMATION: synthetic construct

<400> SEQUENCE: 124
tctttcattc caactaatgt agctagagct taagaggtca tttttgctt          49

<210> SEQ ID NO 125
<211> LENGTH: 49
<212> TYPE: DNA
<213> ORGANISM: Artificial Sequence
<220> FEATURE:
<223> OTHER INFORMATION: synthetic construct

<400> SEQUENCE: 125
cctgattcaa agggcgaaat gggcaagagt ccactattaa agaacgttt          49

<210> SEQ ID NO 126
<211> LENGTH: 49
<212> TYPE: DNA
<213> ORGANISM: Artificial Sequence
<220> FEATURE:
<223> OTHER INFORMATION: synthetic construct

<400> SEQUENCE: 126
ttctattaat taattttccc ttagaacaaa taaccagaaa gagcttgcg          49

<210> SEQ ID NO 127
<211> LENGTH: 56
<212> TYPE: DNA
<213> ORGANISM: Artificial Sequence
<220> FEATURE:
<223> OTHER INFORMATION: synthetic construct

<400> SEQUENCE: 127
tgaacacata tcagagagaa ataaaggtca taaagattca aagggtgag aaagtt    56

<210> SEQ ID NO 128
<211> LENGTH: 22
<212> TYPE: DNA
<213> ORGANISM: Artificial Sequence
<220> FEATURE:
<223> OTHER INFORMATION: synthetic construct

<400> SEQUENCE: 128
ttaccacatt ctacgaggca tt                                       22

<210> SEQ ID NO 129
<211> LENGTH: 22
<212> TYPE: DNA
<213> ORGANISM: Artificial Sequence
<220> FEATURE:
<223> OTHER INFORMATION: synthetic construct

<400> SEQUENCE: 129
ttattaaacg gacctaaaac tt                                       22

<210> SEQ ID NO 130
```

```
<211> LENGTH: 21
<212> TYPE: DNA
<213> ORGANISM: Artificial Sequence
<220> FEATURE:
<223> OTHER INFORMATION: synthetic construct

<400> SEQUENCE: 130
ttaggaggtt tagtaccgcc a                                              21

<210> SEQ ID NO 131
<211> LENGTH: 22
<212> TYPE: DNA
<213> ORGANISM: Artificial Sequence
<220> FEATURE:
<223> OTHER INFORMATION: synthetic construct

<400> SEQUENCE: 131
ttgtagcaac gtagaaagga tt                                             22

<210> SEQ ID NO 132
<211> LENGTH: 25
<212> TYPE: DNA
<213> ORGANISM: Artificial Sequence
<220> FEATURE:
<223> OTHER INFORMATION: synthetic construct

<400> SEQUENCE: 132
ttttctaaga ataacataa aaatt                                           25

<210> SEQ ID NO 133
<211> LENGTH: 25
<212> TYPE: DNA
<213> ORGANISM: Artificial Sequence
<220> FEATURE:
<223> OTHER INFORMATION: synthetic construct

<400> SEQUENCE: 133
ttgcattttc ggtcataatc aaatt                                          25

<210> SEQ ID NO 134
<211> LENGTH: 25
<212> TYPE: DNA
<213> ORGANISM: Artificial Sequence
<220> FEATURE:
<223> OTHER INFORMATION: synthetic construct

<400> SEQUENCE: 134
ttaccaacgc tttacaaaat aaatt                                          25

<210> SEQ ID NO 135
<211> LENGTH: 25
<212> TYPE: DNA
<213> ORGANISM: Artificial Sequence
<220> FEATURE:
<223> OTHER INFORMATION: synthetic construct

<400> SEQUENCE: 135
ttctaacaac ttgaggattt agatt                                          25

<210> SEQ ID NO 136
<211> LENGTH: 25
<212> TYPE: DNA
<213> ORGANISM: Artificial Sequence
<220> FEATURE:
<223> OTHER INFORMATION: synthetic construct

<400> SEQUENCE: 136
```
ttcagtgaga ccctgagaga gtttt                                      25

<210> SEQ ID NO 137
<211> LENGTH: 25
<212> TYPE: DNA
<213> ORGANISM: Artificial Sequence
<220> FEATURE:
<223> OTHER INFORMATION: synthetic construct

<400> SEQUENCE: 137
ttaatcaaca gttgttagga gcatt                                      25

<210> SEQ ID NO 138
<211> LENGTH: 25
<212> TYPE: DNA
<213> ORGANISM: Artificial Sequence
<220> FEATURE:
<223> OTHER INFORMATION: synthetic construct

<400> SEQUENCE: 138
ttcagccata ttatccctttt ttatt                                     25

<210> SEQ ID NO 139
<211> LENGTH: 25
<212> TYPE: DNA
<213> ORGANISM: Artificial Sequence
<220> FEATURE:
<223> OTHER INFORMATION: synthetic construct

<400> SEQUENCE: 139
ttcttaaatc aattttttgt ttatt                                      25

<210> SEQ ID NO 140
<211> LENGTH: 25
<212> TYPE: DNA
<213> ORGANISM: Artificial Sequence
<220> FEATURE:
<223> OTHER INFORMATION: synthetic construct

<400> SEQUENCE: 140
ttccgcctgc aaaaatctaa agctt                                      25

<210> SEQ ID NO 141
<211> LENGTH: 25
<212> TYPE: DNA
<213> ORGANISM: Artificial Sequence
<220> FEATURE:
<223> OTHER INFORMATION: synthetic construct

<400> SEQUENCE: 141
ttagtacata aatctttagg aattt                                      25

<210> SEQ ID NO 142
<211> LENGTH: 25
<212> TYPE: DNA
<213> ORGANISM: Artificial Sequence
<220> FEATURE:
<223> OTHER INFORMATION: synthetic construct

<400> SEQUENCE: 142
ttgcagcaag cggtggaacg aggtt                                      25

<210> SEQ ID NO 143
<211> LENGTH: 25
<212> TYPE: DNA

<210> SEQ ID NO 143
<211> LENGTH: 25
<212> TYPE: DNA
<213> ORGANISM: Artificial Sequence
<220> FEATURE:
<223> OTHER INFORMATION: synthetic construct

<400> SEQUENCE: 143
ttacagaatc aagtcaccct cagtt                                               25

<210> SEQ ID NO 144
<211> LENGTH: 25
<212> TYPE: DNA
<213> ORGANISM: Artificial Sequence
<220> FEATURE:
<223> OTHER INFORMATION: synthetic construct

<400> SEQUENCE: 144
ttagactgga ttcggaacct atttt                                               25

<210> SEQ ID NO 145
<211> LENGTH: 25
<212> TYPE: DNA
<213> ORGANISM: Artificial Sequence
<220> FEATURE:
<223> OTHER INFORMATION: synthetic construct

<400> SEQUENCE: 145
ttttgacgga ataatcagta gcgtt                                               25

<210> SEQ ID NO 146
<211> LENGTH: 25
<212> TYPE: DNA
<213> ORGANISM: Artificial Sequence
<220> FEATURE:
<223> OTHER INFORMATION: synthetic construct

<400> SEQUENCE: 146
ttccgccgcc attggccttg atatt                                               25

<210> SEQ ID NO 147
<211> LENGTH: 25
<212> TYPE: DNA
<213> ORGANISM: Artificial Sequence
<220> FEATURE:
<223> OTHER INFORMATION: synthetic construct

<400> SEQUENCE: 147
tttagtaaga gataagtgcc gtctt                                               25

<210> SEQ ID NO 148
<211> LENGTH: 25
<212> TYPE: DNA
<213> ORGANISM: Artificial Sequence
<220> FEATURE:
<223> OTHER INFORMATION: synthetic construct

<400> SEQUENCE: 148
ttcaataata acgggagcca ttttt                                               25

<210> SEQ ID NO 149
<211> LENGTH: 25
<212> TYPE: DNA
<213> ORGANISM: Artificial Sequence
<220> FEATURE:
<223> OTHER INFORMATION: synthetic construct

<400> SEQUENCE: 149
ttcaaatgct tgccttgagt aactt                                               25

```
<210> SEQ ID NO 150
<211> LENGTH: 25
<212> TYPE: DNA
<213> ORGANISM: Artificial Sequence
<220> FEATURE:
<223> OTHER INFORMATION: synthetic construct

<400> SEQUENCE: 150
ttgaaacgtc accaccacca gagtt                                              25

<210> SEQ ID NO 151
<211> LENGTH: 25
<212> TYPE: DNA
<213> ORGANISM: Artificial Sequence
<220> FEATURE:
<223> OTHER INFORMATION: synthetic construct

<400> SEQUENCE: 151
ttaaccgcca cgaaagcgca gtctt                                              25

<210> SEQ ID NO 152
<211> LENGTH: 25
<212> TYPE: DNA
<213> ORGANISM: Artificial Sequence
<220> FEATURE:
<223> OTHER INFORMATION: synthetic construct

<400> SEQUENCE: 152
ttttacgcag tatgaggtaa atatt                                              25

<210> SEQ ID NO 153
<211> LENGTH: 25
<212> TYPE: DNA
<213> ORGANISM: Artificial Sequence
<220> FEATURE:
<223> OTHER INFORMATION: synthetic construct

<400> SEQUENCE: 153
tttagcgaga gctcaagaga aggtt                                              25

<210> SEQ ID NO 154
<211> LENGTH: 25
<212> TYPE: DNA
<213> ORGANISM: Artificial Sequence
<220> FEATURE:
<223> OTHER INFORMATION: synthetic construct

<400> SEQUENCE: 154
ttgggtaatt ggaaacgcaa agatt                                              25

<210> SEQ ID NO 155
<211> LENGTH: 25
<212> TYPE: DNA
<213> ORGANISM: Artificial Sequence
<220> FEATURE:
<223> OTHER INFORMATION: synthetic construct

<400> SEQUENCE: 155
ttacaacgcc aagtaataag agatt                                              25

<210> SEQ ID NO 156
<211> LENGTH: 25
<212> TYPE: DNA
<213> ORGANISM: Artificial Sequence
<220> FEATURE:
```

```
<223> OTHER INFORMATION: synthetic construct

<400> SEQUENCE: 156
ttcagggaag cgcaaaagtc agatt                                         25

<210> SEQ ID NO 157
<211> LENGTH: 25
<212> TYPE: DNA
<213> ORGANISM: Artificial Sequence
<220> FEATURE:
<223> OTHER INFORMATION: synthetic construct

<400> SEQUENCE: 157
ttgaaagagg catcaccgta ctctt                                         25

<210> SEQ ID NO 158
<211> LENGTH: 25
<212> TYPE: DNA
<213> ORGANISM: Artificial Sequence
<220> FEATURE:
<223> OTHER INFORMATION: synthetic construct

<400> SEQUENCE: 158
ttccagcgcc agcgttttca tcgtt                                         25

<210> SEQ ID NO 159
<211> LENGTH: 25
<212> TYPE: DNA
<213> ORGANISM: Artificial Sequence
<220> FEATURE:
<223> OTHER INFORMATION: synthetic construct

<400> SEQUENCE: 159
ttagtattag acttgaagtt tcctt                                         25

<210> SEQ ID NO 160
<211> LENGTH: 25
<212> TYPE: DNA
<213> ORGANISM: Artificial Sequence
<220> FEATURE:
<223> OTHER INFORMATION: synthetic construct

<400> SEQUENCE: 160
ttcaccacgg aatatatggt ttatt                                         25

<210> SEQ ID NO 161
<211> LENGTH: 25
<212> TYPE: DNA
<213> ORGANISM: Artificial Sequence
<220> FEATURE:
<223> OTHER INFORMATION: synthetic construct

<400> SEQUENCE: 161
tttcctaatt tgtctttcct tattt                                         25

<210> SEQ ID NO 162
<211> LENGTH: 25
<212> TYPE: DNA
<213> ORGANISM: Artificial Sequence
<220> FEATURE:
<223> OTHER INFORMATION: synthetic construct

<400> SEQUENCE: 162
ttgcgcgggg agagtctttt cactt                                         25
```

```
<210> SEQ ID NO 163
<211> LENGTH: 25
<212> TYPE: DNA
<213> ORGANISM: Artificial Sequence
<220> FEATURE:
<223> OTHER INFORMATION: synthetic construct

<400> SEQUENCE: 163
ttagaaaagt aaccgaggaa acgtt                                           25

<210> SEQ ID NO 164
<211> LENGTH: 25
<212> TYPE: DNA
<213> ORGANISM: Artificial Sequence
<220> FEATURE:
<223> OTHER INFORMATION: synthetic construct

<400> SEQUENCE: 164
ttcaaaatta atttaatgga aactt                                           25

<210> SEQ ID NO 165
<211> LENGTH: 25
<212> TYPE: DNA
<213> ORGANISM: Artificial Sequence
<220> FEATURE:
<223> OTHER INFORMATION: synthetic construct

<400> SEQUENCE: 165
tttaacgtca gggagaaaca atatt                                           25

<210> SEQ ID NO 166
<211> LENGTH: 25
<212> TYPE: DNA
<213> ORGANISM: Artificial Sequence
<220> FEATURE:
<223> OTHER INFORMATION: synthetic construct

<400> SEQUENCE: 166
ttattcattt caattcaaga aaatt                                           25

<210> SEQ ID NO 167
<211> LENGTH: 25
<212> TYPE: DNA
<213> ORGANISM: Artificial Sequence
<220> FEATURE:
<223> OTHER INFORMATION: synthetic construct

<400> SEQUENCE: 167
ttgggaatta gttagcaagg ccgtt                                           25

<210> SEQ ID NO 168
<211> LENGTH: 25
<212> TYPE: DNA
<213> ORGANISM: Artificial Sequence
<220> FEATURE:
<223> OTHER INFORMATION: synthetic construct

<400> SEQUENCE: 168
ttacgtcaaa aatgtaagcc caatt                                           25

<210> SEQ ID NO 169
<211> LENGTH: 25
<212> TYPE: DNA
<213> ORGANISM: Artificial Sequence
<220> FEATURE:
<223> OTHER INFORMATION: synthetic construct
```

<400> SEQUENCE: 169
ttgcctgggg tgttgcgctc acttt                                    25

<210> SEQ ID NO 170
<211> LENGTH: 25
<212> TYPE: DNA
<213> ORGANISM: Artificial Sequence
<220> FEATURE:
<223> OTHER INFORMATION: synthetic construct

<400> SEQUENCE: 170
ttatcaccgg attttgatga tactt                                    25

<210> SEQ ID NO 171
<211> LENGTH: 25
<212> TYPE: DNA
<213> ORGANISM: Artificial Sequence
<220> FEATURE:
<223> OTHER INFORMATION: synthetic construct

<400> SEQUENCE: 171
ttacaactaa actcagaacc gcctt                                    25

<210> SEQ ID NO 172
<211> LENGTH: 25
<212> TYPE: DNA
<213> ORGANISM: Artificial Sequence
<220> FEATURE:
<223> OTHER INFORMATION: synthetic construct

<400> SEQUENCE: 172
tttctgacct aaaataaggc gtttt                                    25

<210> SEQ ID NO 173
<211> LENGTH: 25
<212> TYPE: DNA
<213> ORGANISM: Artificial Sequence
<220> FEATURE:
<223> OTHER INFORMATION: synthetic construct

<400> SEQUENCE: 173
tttaataaga gtaagactcc ttatt                                    25

<210> SEQ ID NO 174
<211> LENGTH: 28
<212> TYPE: DNA
<213> ORGANISM: Artificial Sequence
<220> FEATURE:
<223> OTHER INFORMATION: synthetic construct

<400> SEQUENCE: 174
ttacggattc gcctcagagg cgaatttt                                 28

<210> SEQ ID NO 175
<211> LENGTH: 28
<212> TYPE: DNA
<213> ORGANISM: Artificial Sequence
<220> FEATURE:
<223> OTHER INFORMATION: synthetic construct

<400> SEQUENCE: 175
ttgcccgctt tccagaatcg gccaactt                                 28

<210> SEQ ID NO 176
<211> LENGTH: 28

<212> TYPE: DNA
<213> ORGANISM: Artificial Sequence
<220> FEATURE:
<223> OTHER INFORMATION: synthetic construct

<400> SEQUENCE: 176
ttatcacctt gctgggtcag ttggcatt                                    28

<210> SEQ ID NO 177
<211> LENGTH: 32
<212> TYPE: DNA
<213> ORGANISM: Artificial Sequence
<220> FEATURE:
<223> OTHER INFORMATION: synthetic construct

<400> SEQUENCE: 177
gcctattagc gtcctaatag taaaatgttt tt                               32

<210> SEQ ID NO 178
<211> LENGTH: 32
<212> TYPE: DNA
<213> ORGANISM: Artificial Sequence
<220> FEATURE:
<223> OTHER INFORMATION: synthetic construct

<400> SEQUENCE: 178
ggtcagttaa acagttcatt gaatcccct tt                                32

<210> SEQ ID NO 179
<211> LENGTH: 32
<212> TYPE: DNA
<213> ORGANISM: Artificial Sequence
<220> FEATURE:
<223> OTHER INFORMATION: synthetic construct

<400> SEQUENCE: 179
gagactcgct tttgacgata aaaccaaaa tt                                32

<210> SEQ ID NO 180
<211> LENGTH: 35
<212> TYPE: DNA
<213> ORGANISM: Artificial Sequence
<220> FEATURE:
<223> OTHER INFORMATION: synthetic construct

<400> SEQUENCE: 180
ttttatccgc tcacaattcc acacaatgtc atagc                            35

<210> SEQ ID NO 181
<211> LENGTH: 35
<212> TYPE: DNA
<213> ORGANISM: Artificial Sequence
<220> FEATURE:
<223> OTHER INFORMATION: synthetic construct

<400> SEQUENCE: 181
ttattctgaa acatgaaagt attaagcaac cccct                            35

<210> SEQ ID NO 182
<211> LENGTH: 35
<212> TYPE: DNA
<213> ORGANISM: Artificial Sequence
<220> FEATURE:
<223> OTHER INFORMATION: synthetic construct

<400> SEQUENCE: 182
ttttcacaaa caaataaatc ctcattacgg caggt         35

<210> SEQ ID NO 183
<211> LENGTH: 35
<212> TYPE: DNA
<213> ORGANISM: Artificial Sequence
<220> FEATURE:
<223> OTHER INFORMATION: synthetic construct

<400> SEQUENCE: 183
ttaggagtgt actggtaata agttttcaat gtcat         35

<210> SEQ ID NO 184
<211> LENGTH: 35
<212> TYPE: DNA
<213> ORGANISM: Artificial Sequence
<220> FEATURE:
<223> OTHER INFORMATION: synthetic construct

<400> SEQUENCE: 184
ttattaggat tagcggggtt ttgctcgtgt aggct         35

<210> SEQ ID NO 185
<211> LENGTH: 35
<212> TYPE: DNA
<213> ORGANISM: Artificial Sequence
<220> FEATURE:
<223> OTHER INFORMATION: synthetic construct

<400> SEQUENCE: 185
ttagtgcccg tataaacagt taatgcagat aacgg         35

<210> SEQ ID NO 186
<211> LENGTH: 38
<212> TYPE: DNA
<213> ORGANISM: Artificial Sequence
<220> FEATURE:
<223> OTHER INFORMATION: synthetic construct

<400> SEQUENCE: 186
tttgtaacac cctcatagtt tcagggatag caagcctt         38

<210> SEQ ID NO 187
<211> LENGTH: 39
<212> TYPE: DNA
<213> ORGANISM: Artificial Sequence
<220> FEATURE:
<223> OTHER INFORMATION: synthetic construct

<400> SEQUENCE: 187
ttcaatagga acccatgtac ccagcggacg aataactac         39

<210> SEQ ID NO 188
<211> LENGTH: 45
<212> TYPE: DNA
<213> ORGANISM: Artificial Sequence
<220> FEATURE:
<223> OTHER INFORMATION: synthetic construct

<400> SEQUENCE: 188
gataatatct aaaggaacat taatgtcggg atgtgtgaaa ttgtt         45

<210> SEQ ID NO 189
<211> LENGTH: 46
<212> TYPE: DNA
<213> ORGANISM: Artificial Sequence
<220> FEATURE:
<223> OTHER INFORMATION: synthetic construct

<400> SEQUENCE: 189
cagcccatga aataagaaac gagattagcg ggaggttttg aagctt                46

<210> SEQ ID NO 190
<211> LENGTH: 46
<212> TYPE: DNA
<213> ORGANISM: Artificial Sequence
<220> FEATURE:
<223> OTHER INFORMATION: synthetic construct

<400> SEQUENCE: 190
aatccaggcc taatttgcca gaacgagctt ttatcctgaa tctttt                46

<210> SEQ ID NO 191
<211> LENGTH: 46
<212> TYPE: DNA
<213> ORGANISM: Artificial Sequence
<220> FEATURE:
<223> OTHER INFORMATION: synthetic construct

<400> SEQUENCE: 191
aatcgcggat tgctcaaatg aacagtgcgc ggtcagtatt aacatt                46

<210> SEQ ID NO 192
<211> LENGTH: 46
<212> TYPE: DNA
<213> ORGANISM: Artificial Sequence
<220> FEATURE:
<223> OTHER INFORMATION: synthetic construct

<400> SEQUENCE: 192
ttaccctcag agccaccacc ctcatttaca agaaccgcca ccggaa                46

<210> SEQ ID NO 193
<211> LENGTH: 46
<212> TYPE: DNA
<213> ORGANISM: Artificial Sequence
<220> FEATURE:
<223> OTHER INFORMATION: synthetic construct

<400> SEQUENCE: 193
tttctgaatt taccgttcca gtaagctaga aaagccagaa tgcctc                46

<210> SEQ ID NO 194
<211> LENGTH: 46
<212> TYPE: DNA
<213> ORGANISM: Artificial Sequence
<220> FEATURE:
<223> OTHER INFORMATION: synthetic construct

<400> SEQUENCE: 194
ttgagagggt tgatataagt atagccttt agtaccaggc ggcaac                 46

<210> SEQ ID NO 195
<211> LENGTH: 49
<212> TYPE: DNA
<213> ORGANISM: Artificial Sequence
<220> FEATURE:
<223> OTHER INFORMATION: synthetic construct

<400> SEQUENCE: 195
tgaaatatct aacctcataa ttgcgcctaa taagcataaa gtgtaaatt             49

<210> SEQ ID NO 196
<211> LENGTH: 49
<212> TYPE: DNA
<213> ORGANISM: Artificial Sequence
<220> FEATURE:
<223> OTHER INFORMATION: synthetic construct

<400> SEQUENCE: 196
ataggagaat attttacaga gagacgcgag ggaaggctta tccggtatt                49

<210> SEQ ID NO 197
<211> LENGTH: 49
<212> TYPE: DNA
<213> ORGANISM: Artificial Sequence
<220> FEATURE:
<223> OTHER INFORMATION: synthetic construct

<400> SEQUENCE: 197
ctacctgaac ttagacgatc ggctacgagc agaaaaataa tatcccatt                49

<210> SEQ ID NO 198
<211> LENGTH: 53
<212> TYPE: DNA
<213> ORGANISM: Artificial Sequence
<220> FEATURE:
<223> OTHER INFORMATION: synthetic construct

<400> SEQUENCE: 198
ttaaataaga ataaacaccg gtacatcgat gaatacgtag attttcaggt ttt           53

<210> SEQ ID NO 199
<211> LENGTH: 53
<212> TYPE: DNA
<213> ORGANISM: Artificial Sequence
<220> FEATURE:
<223> OTHER INFORMATION: synthetic construct

<400> SEQUENCE: 199
ttatataaag taccgacaaa agtgtgataa tttaattagt taatttcatc ttt           53

<210> SEQ ID NO 200
<211> LENGTH: 53
<212> TYPE: DNA
<213> ORGANISM: Artificial Sequence
<220> FEATURE:
<223> OTHER INFORMATION: synthetic construct

<400> SEQUENCE: 200
ttcattccaa gaacgggtat ttcgagccac atgtaagaat cgccatattt att           53

<210> SEQ ID NO 201
<211> LENGTH: 40
<212> TYPE: DNA
<213> ORGANISM: Artificial Sequence
<220> FEATURE:
<223> OTHER INFORMATION: synthetic construct

<400> SEQUENCE: 201
aacattttta gtaatgtgta ggatgaaaaa aaaaaaaaaa                          40

<210> SEQ ID NO 202
<211> LENGTH: 40
<212> TYPE: DNA
<213> ORGANISM: Artificial Sequence
<220> FEATURE:
<223> OTHER INFORMATION: synthetic construct

<400> SEQUENCE: 202
cgaatagata gtgagtgttt gaatgaaaaa aaaaaaaaaa         40

<210> SEQ ID NO 203
<211> LENGTH: 41
<212> TYPE: DNA
<213> ORGANISM: Artificial Sequence
<220> FEATURE:
<223> OTHER INFORMATION: synthetic construct

<400> SEQUENCE: 203
ctaatagagc ctgatgaata acaatgaaaa aaaaaaaaa a         41

<210> SEQ ID NO 204
<211> LENGTH: 44
<212> TYPE: DNA
<213> ORGANISM: Artificial Sequence
<220> FEATURE:
<223> OTHER INFORMATION: synthetic construct

<400> SEQUENCE: 204
acatggcacc agagtctttt catagcccga aaaaaaaaaa aaaa         44

<210> SEQ ID NO 205
<211> LENGTH: 44
<212> TYPE: DNA
<213> ORGANISM: Artificial Sequence
<220> FEATURE:
<223> OTHER INFORMATION: synthetic construct

<400> SEQUENCE: 205
gacttttacg taatttcatc agcagataga aaaaaaaaaa aaaa         44

<210> SEQ ID NO 206
<211> LENGTH: 44
<212> TYPE: DNA
<213> ORGANISM: Artificial Sequence
<220> FEATURE:
<223> OTHER INFORMATION: synthetic construct

<400> SEQUENCE: 206
gggaaccacg aggcagtaaa tcattgtgga aaaaaaaaaa aaaa         44

<210> SEQ ID NO 207
<211> LENGTH: 44
<212> TYPE: DNA
<213> ORGANISM: Artificial Sequence
<220> FEATURE:
<223> OTHER INFORMATION: synthetic construct

<400> SEQUENCE: 207
actcatcgct aatgcagaag ataattctca aaaaaaaaaa aaaa         44

<210> SEQ ID NO 208
<211> LENGTH: 44
<212> TYPE: DNA
<213> ORGANISM: Artificial Sequence
<220> FEATURE:
<223> OTHER INFORMATION: synthetic construct

<400> SEQUENCE: 208
gtccagaaca aattcttaca tattactaca aaaaaaaaaa aaaa         44

<210> SEQ ID NO 209
<211> LENGTH: 44
<212> TYPE: DNA
<213> ORGANISM: Artificial Sequence
<220> FEATURE:
<223> OTHER INFORMATION: synthetic construct

<400> SEQUENCE: 209 taaattttc atcgtaggac agtaccgcga aaaaaaaaa aaaa                44

<210> SEQ ID NO 210
<211> LENGTH: 47
<212> TYPE: DNA
<213> ORGANISM: Artificial Sequence
<220> FEATURE:
<223> OTHER INFORMATION: synthetic construct

<400> SEQUENCE: 210
acgagtagcg aacgagaatg acttcgtaac agaaaaaaaa aaaaaaa          47

<210> SEQ ID NO 211
<211> LENGTH: 58
<212> TYPE: DNA
<213> ORGANISM: Artificial Sequence
<220> FEATURE:
<223> OTHER INFORMATION: synthetic construct

<400> SEQUENCE: 211
gcgtattcca gctgttgagg actcaatcgc aaaaggttac aagaaaaaaa aaaaaaaa    58

<210> SEQ ID NO 212
<211> LENGTH: 58
<212> TYPE: DNA
<213> ORGANISM: Artificial Sequence
<220> FEATURE:
<223> OTHER INFORMATION: synthetic construct

<400> SEQUENCE: 212
atcaaaaacc aggcgcatag gcagatgatg ctcatccaga accaaaaaaa aaaaaaaa    58

<210> SEQ ID NO 213
<211> LENGTH: 58
<212> TYPE: DNA
<213> ORGANISM: Artificial Sequence
<220> FEATURE:
<223> OTHER INFORMATION: synthetic construct

<400> SEQUENCE: 213
ccttattgct cagactgtag caagacaaaa attcaagttt atgaaaaaaa aaaaaaaa    58

<210> SEQ ID NO 214
<211> LENGTH: 58
<212> TYPE: DNA
<213> ORGANISM: Artificial Sequence
<220> FEATURE:
<223> OTHER INFORMATION: synthetic construct

<400> SEQUENCE: 214
ttgccggaga cagtcaaatc agattgtatt tgttaaaatt acgaaaaaaa aaaaaaaa    58

<210> SEQ ID NO 215
<211> LENGTH: 15
<212> TYPE: DNA
<213> ORGANISM: Artificial Sequence
<220> FEATURE:
<223> OTHER INFORMATION: synthetic construct

```
<400> SEQUENCE: 215 ttttttttttt ttttt                                             15

<210> SEQ ID NO 216
<211> LENGTH: 40
<212> TYPE: DNA
<213> ORGANISM: Artificial Sequence
<220> FEATURE:
<223> OTHER INFORMATION: synthetic construct

<400> SEQUENCE: 216
tgagtagaag aactcaaact atcggccttg ctggtaatat                   40

<210> SEQ ID NO 217
<211> LENGTH: 15
<212> TYPE: DNA
<213> ORGANISM: Artificial Sequence
<220> FEATURE:
<223> OTHER INFORMATION: synthetic construct

<400> SEQUENCE: 217
aaaaaaaaaa aaaaa                                              15
```

LIGHT-STIMULATED RELEASE OF CARGO FROM OLIGONUCLEOTIDES

STATEMENT REGARDING FEDERALLY SPONSORED RESEARCH

This invention was made with Government Support under Contract No. NS082126 awarded by the National Institutes of Health. The Government has certain rights in the invention.

BACKGROUND OF THE INVENTION

A general platform that could release a vast number of bioactive molecules with light would be of great interest to the neuroscience community. Currently neuroscientists buy caged neurotransmitters from commercial sources, but the number of compounds available is small relative to the amount of compounds that would like to be explored. Accordingly, there is a need for new crosslinking strategies in neuroscience and other fields.

SUMMARY OF THE INVENTION

The invention provides an oligonucleotide conjugate including an oligonucleotide, e.g., of 2-1000 nucleotides in length, such as 2-200 or 2-100 nucleotides in length, conjugated to a therapeutic or diagnostic agent by a photolabile linker, wherein upon suitable illumination, the therapeutic or diagnostic agent dissociates from the oligonucleotide.

In one aspect, the invention provides an oligonucleotide conjugate of the formula:

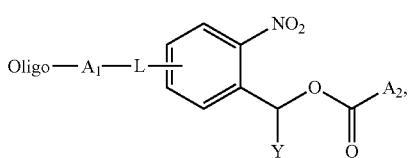

wherein Oligo is an oligonucleotide, e.g., of 2-1000 nucleotides in length, such as 2-200 or 2-100 nucleotides in length, $A_1$ is the residue of a conjugation reaction, $A_2$ is an amine reactive leaving group or —NHX, L is an optional linker, Y is H or C1-10 alkyl, and X is a cargo moiety. In certain embodiments, L is present and is amido (—NHC(O)—), C1-10 alkylene or C1-20 polyalkeneoxide, e.g., C2-C20 polyethylene glycol or —O—CH$_2$—; $A_1$ is triazolyl, disulfide, cyclohexenyl, amido, thioamido (—NHC(S)—), acetal, ketal, or sulfonamide (—NHSO$_2$—); and/or Y is C1-10 alkyl, e.g., methyl. In embodiments wherein $A_2$ is the amine reactive group, examples of such groups include p-nitrophenoxyl, N-hydroxysuccinimidyl, halide, pentafluorophenoxyl, and imidazolyl. In embodiments wherein $A_2$ is —NHX, X may be a therapeutic or diagnostic agent, e.g., as described herein. In particular embodiments, $A_1$ and L are para to the nitro group.

In specific embodiments, the conjugate has the formula:

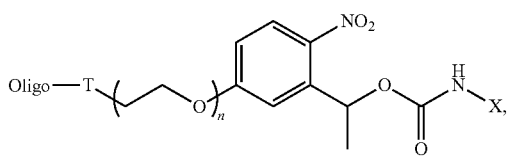

wherein Oligo is an oligonucleotide of 2-100 nucleotides in length, T is a triazolyl linker formed from the reaction of an azide with an alkyne, X is a cargo moiety, and n is an integer from 1-10. In other embodiments, this formula is specifically excluded.

The invention further features a crosslinker of the formula:

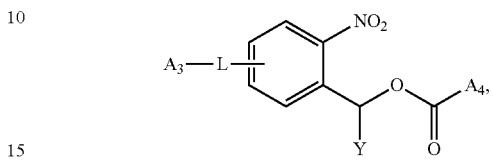

wherein $A_3$ is a conjugating moiety, $A_4$ is an amine reactive leaving group, L is an optional linker, and Y is H or C1-10 alkyl. In certain embodiments, L is present and is amido, C1-10 alkylene or C1-20 polyalkeneoxide, e.g., C2-C20 polyethylene glycol or —O—CH$_2$—; $A_3$ is azido, alkynyl, alkenyl, thiol, halide, boronic acid, hydroxyl, carboxyl, formyl, or ketone; Y is C1-11 alkyl, e.g., methyl; and/or $A_4$ is p-nitrophenoxyl, N-hydroxysuccinimidyl, halide, pentafluorophenoxyl, or imidazolyl. In particular embodiments, $A_3$ and L are para to the nitro group.

In certain embodiments, the crosslinker has the formula:

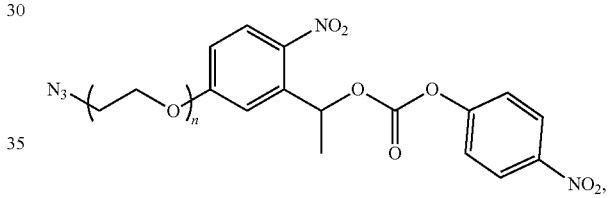

where n is an integer from 1-10. In other embodiments, this formula is specifically excluded.

In a further aspect, the invention provides a DNA construct including a three-dimensional DNA nanostructure, e.g., cage structure, for housing a cargo moiety, wherein the cargo moiety is attached to the cage structure via an oligonucleotide conjugate of the invention.

The invention also provides a method of delivering a cargo moiety by providing a conjugate of the invention and irradiating the conjugate with light to release the cargo moiety, e.g., a therapeutic or diagnostic agent, e.g., as described herein. The conjugate is, for example, internalized within a cell prior to irradiation.

In another aspect, the invention provides a pharmaceutical composition including an oligonucleotide conjugate of the invention and a pharmaceutically acceptable carrier.

BRIEF DESCRIPTION OF THE DRAWINGS

FIGS. 2A-2C. Light-triggered release of small molecules from nanocages. (2A) Photolysis data showing increased irradiation duration results in an increase in the cleavage of Oregon Green/oligonucleotides conjugate. (2B) Schematic depiction of the dye uncaging experiment. DNA nanostructures remain in the microdialysis chamber while small dyes are able to diffuse out. (2C) Absorption spectra of a duel dye tagged nanocage before (yellow curve) and after light irradiation (blue curve).

FIGS. 3A-3B. Light-triggered release of proteins, (3A) Streptavidin and (3B) Bovine Serum Albumin from nanocages. (3Ai, 3Bi) Schematic depictions of the DNA nanocages with and without proteins (3Aii, 3Bii) TEM images of nanocaged proteins before (left) and after (middle) irradiation with light. Scale bars are 25 nm. (3Aiii, 3Biii) Graphs showing percentage of nanocages containing protein as determined by TEM image counting before and after light are shown on the right. Numbers in parenthesis indicate the number of particles counted per condition.

FIGS. 4A-4D. Light-triggered release of glutamate from DNA nanocages. (4A) Schematic depiction of glutamate release from DNA nanocages using UV light at 240-400 nm and the subsequent activation of neurons by the freed glutamate. (4B, 4C) Temporal derivative of the normalized fluorescence intensity indicating calcium concentration changes in the control group, neurons illuminated in the absence of nanocages (4C, N=185 neurons). (4D) Normalized fluorescence intensity indicating intracellular calcium activities of responsive cells in the uncaged group, aligned to light onset. Thick line indicates the mean, shaded area indicates standard deviation, and dots indicate the onset time (N=30 neurons).

FIG. 10A: Structure of glutamate-linker-oligonucleotide complex.

FIG. 10B: Normalized fluorescence intensity of the calcium indicator Fluo-4 in two neurons in the presence of glutamate-linker-oligonucleotide shown in 10A.

DETAILED DESCRIPTION OF THE INVENTION

Figures 1A, 1B, 1C, 1D, 1E:
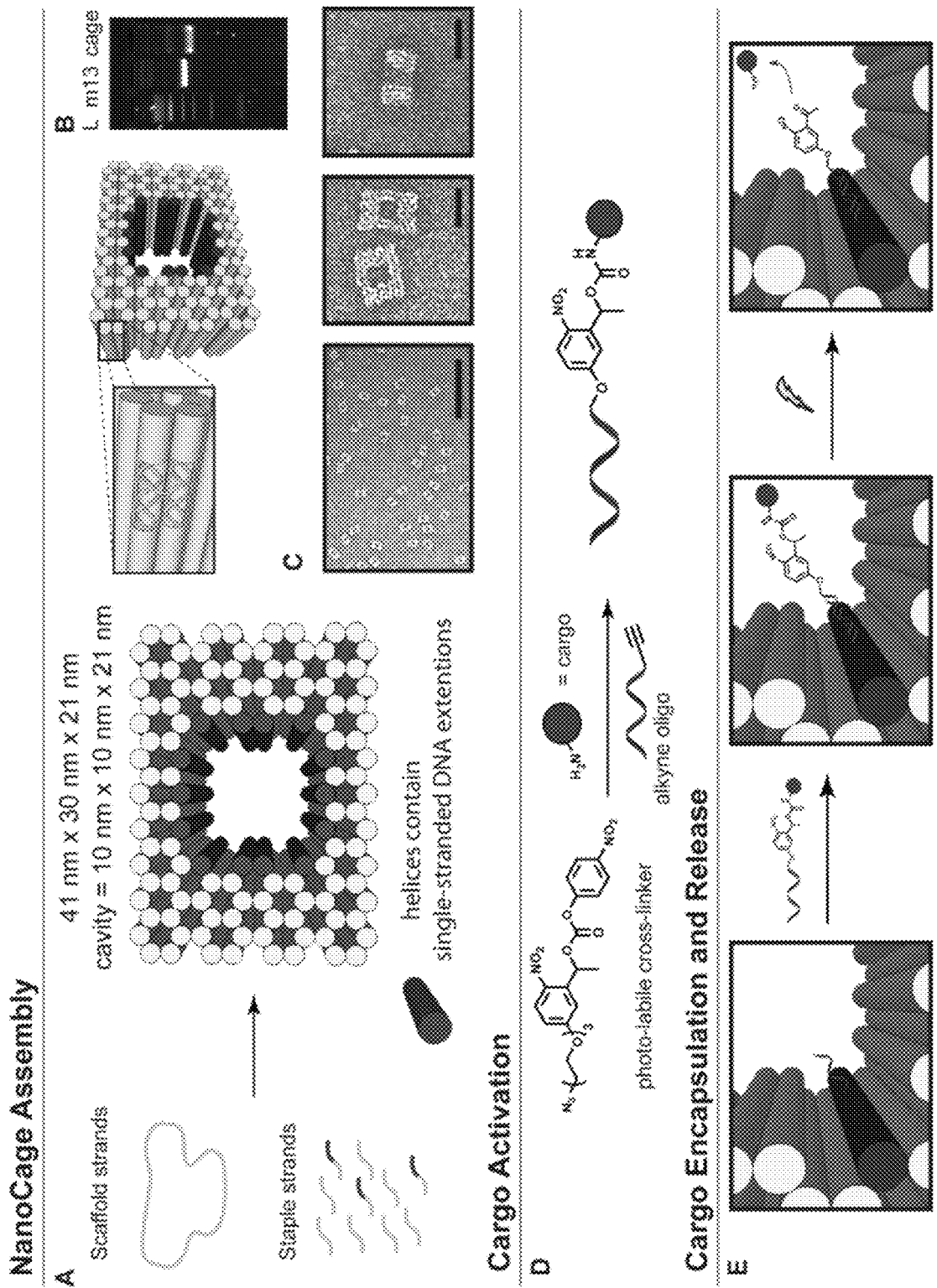
FIGS. 1A-1E. Design and creation of light-triggered, cargo-releasing nanocages. (1A) Scheme of the chemical activation of a cargo molecule with the photolabile crosslinker and an oligonucleotide. (1B) Depiction of the DNA nanostructure formation. The solid cylinders represent DNA helices as shown by the insert. (1C) Agarose gel electrophoresis showing the high folding yield of the crude DNA nanocage sample. Lane L contains the 1-kb ladder, lane m13 contains the single stranded DNA starting material, and lane cage contains the crude reaction mixture. (1D) TEM images of DNA nanocages. Scale bars are 200 and 25 nm respectively. (1E) Schematic depiction of the encapsulation of cargo, the photo-cleavage reaction, and subsequent cargo release.

In general, the invention provides oligonucleotide conjugates containing cargo moieties linked by a photolabile crosslinker. Illumination of the conjugate results in the release of the cargo moiety, which may be a therapeutic or diagnostic agent. This novel molecular uncaging technique offers a general approach for precisely releasing a large variety of bioactive molecules, allowing investigation into their mechanism of action, or finely tuned delivery with high temporal precision for broad biomedical and materials applications.

There is no other technology currently available that can accomplish what this invention does. The delivery platform described here is capable of releasing a large variety of bioactive molecules in a general fashion. There currently are commercially available caged neurotransmitters for a small number of molecules but not for the myriad of compounds that neuroscientists are interested in investigating. Additionally, there are many chemical crosslinkers commercially available but none that are photolabile and release the attached molecules in a chemically unaltered (and thus bioactive) form.

Conjugates

Conjugates of the invention feature an oligonucleotide conjugated to a cargo moiety (or molecule) via a photolabile crosslinker. The conjugates may also include the oligonucleotide conjugated to the crosslinker, which is capable of reaction with the cargo moiety. In one embodiments, the conjugate has the formula:

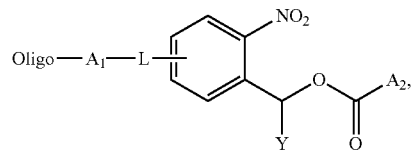

wherein Oligo is an oligonucleotide of 2-1000 nucleotides in length, e.g., 2-200 or 2-100 nucleotides in length, $A_1$ is the residue of a conjugation reaction, $A_2$ is an amine reactive leaving group or —NHX, L is an optional linker, Y is H or C1-10 alkyl, e.g., methyl, and X is a cargo moiety, as described herein. Preferred linkers include amido, C1-10 alkylene, or C1-20 polyalkeneoxide, such as ethylene glycol or —O—$CH_2$—. Suitable conjugation reactions include an azide-alkyne Huisgen cycloaddition (e.g., a copper(I)-catalyzed azide-alkyne cycloaddition (CuAAC) or a strain-promoted azide-alkyne cycloaddition (SPAAC)), amide or thioamide bond formation, a pericyclic reaction, a Diels-Alder reaction, sulfonamide bond formation, alcohol or phenol alkylation, a condensation reaction, disulfide bond formation, and a nucleophilic substitution. An exemplary $A_1$ is triazolyl, disulfide, cyclohexenyl, amido, thioamido, acetal, ketal, or sulfonamido. For $A_2$, any suitable amine reactive leaving group, such as p-nitrophenoxyl, N-hydroxysuccinimidyl, halide, pentafluorophenol, or imidazolyl, may be employed. In certain embodiments, $A_1$ and L are para to the nitro group. In one embodiment, the conjugate has the formula:

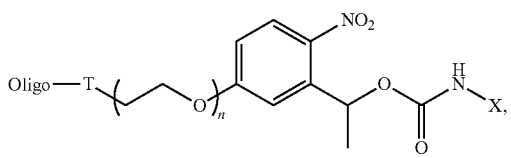

wherein Oligo is an oligonucleotide of 2-100 nucleotides in length, T is a triazolyl linker formed from the reaction of an azide with an alkyne, X is a cargo moiety, and n is an integer from 1-10.

Oligonucleotides

Any oligonucleotide, e.g., of 2 to 1000 nucleotides in length (such as 2 to 200 or 2 to 100 nucleotides in length), may be employed in the present invention. The term encompasses, for example, deoxyribonucleic acid (DNA), ribonucleic acid (RNA), hybrids thereof, and mixtures thereof. Oligonucleotides are typically linked in a nucleic acid by phosphodiester bonds, although the term also encompasses nucleic acid analogs having other types of linkages or backbones (e.g., phosphoramide, phosphorothioate, phosphorodithioate, O-methylphosphoroamidate, morpholino, locked nucleic acid (LNA), glycerol nucleic acid (GNA), threose nucleic acid (TNA), and peptide nucleic acid (PNA) linkages or backbones, among others). The oligonucleotides may be single-stranded, double-stranded, or contain portions of both single-stranded and double-stranded sequence. A nucleic acid can contain any combination of deoxyribonucleotides and ribonucleotides, as well as any combination of bases, including, for example, adenine, thymine, cytosine, guanine, uracil, and modified or non-canonical bases (including, e.g., hypoxanthine, xanthine, 7-methylguanine, 5,6-dihydrouracil, 5-methylcytosine, and 5-hydroxymethylcytosine). In addition, oligonucleotides may form a specific structure, e.g., as in an aptamer, or be part of a larger structure, e.g., a DNA nanostructure. Oligonucleotides can be modified as is known in the art to includes moieties that participate in conjugation reactions as described herein.

Recent innovations in DNA nanofabrication allow the creation of intricately shaped nanostructures ideally suited for many biological applications. To advance the use of DNA nanotechnology for the controlled release of bioactive molecules, we report a general strategy that uses light to liberate encapsulated cargoes from DNA nanostructures with high spatiotemporal precision. Suitable DNA nanostructures include cage structures with interior voids where a cargo moiety can be attached.

Cargo Moieties

Cargo moieties may be any suitable agent for controlled release from a conjugate of the invention. Examples include therapeutic and diagnostic agents, such as peptides, proteins, carbohydrates, other oligonucleotides, small molecules (e.g., neurotransmitters, vitamins, ligands, amino acids, and drugs), contrast agents, and dyes. Typically, the cargo moiety will be attached to the crosslinker by an amine group naturally present in the cargo moiety. For example, proteins typically have free amine groups available for conjugation. Alternatively, an amine group may be introduced into the cargo moiety by methods known in the art. Other attachments, however, are encompassed by the invention.

Photolabile Crosslinkers

Photolabile crosslinkers are known in the art. A preferred crosslinker employs an o-nitrobenzyl moiety. Crosslinkers can be conjugated to the oligonucleotide and to the cargo moiety by orthogonal chemistries, i.e., different reactions that result in attachment of the oligonucleotide at a designated end of the crosslinker and the cargo moiety at the other end. In some instances, the crosslinkers can be conjugated to the oligonucleotide or cargo moiety by an azide-alkyne Huisgen cycloaddition (e.g., a copper(I)-catalyzed azide-alkyne cycloaddition (CuAAC) or a strain-promoted azide-alkyne cycloaddition (SPAAC)), amide or thioamide bond formation, a pericyclic reaction, a Diels-Alder reaction, sulfonamide bond formation, alcohol or phenol alkylation, a condensation reaction, disulfide bond formation, and a nucleophilic substitution. Preferably, the cargo moiety is attached to the crosslinker via an amine group in the cargo moiety.

In one embodiment, the crosslinker has the following formula:

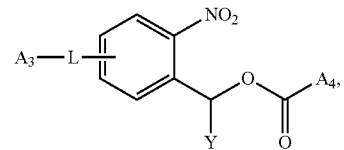

wherein $A_3$ is a conjugating moiety, $A_4$ is an amine reactive leaving group, L is an optional linker, and Y is H or C1-10 alkyl, e.g., methyl. Preferred linkers include amido, C1-10 alkylene, or C1-20 polyalkeneoxide, such as ethylene glycol or —O—CH$_2$—. Suitable conjugating moieties for $A_3$ include those capable of participating in the conjugation reactions discussed above, e.g., an azide, an alkyne (e.g., cyclooctyne), a diene, a dienophile, a thiol, an alkene, a halide, a boronic acid, hydroxyl, carboxyl, formyl, or ketone. For $A_4$, any suitable amine reactive leaving group, such as p-nitrophenoxyl, N-hydroxysuccinimidyl, halide, pentafluorophenol, or imidazolyl, may be employed. In certain embodiments, $A_3$ and L are para to the nitro group. An exemplary crosslinker has the formula:

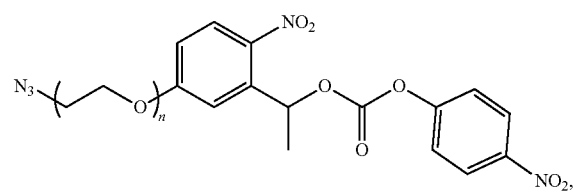

where n is an integer from 1-10.

Methods of Use

The conjugates of the invention may be employed to deliver cargo moieties to locations of interest. Once delivery, the cargo moiety can be released from the conjugate via illumination with the appropriate wavelength of light. The wavelength and duration of the illumination can be determined by one of skill in the art. Without being bound by theory, the conjugates can increase the stability of the cargo moiety by protecting the cargo from degradation or elimination. The conjugate can also prevent the cargo moiety from being active until release. The conjugates may be deployed to deliver the cargo moiety in vivo or ex vivo. The conjugate can be delivery topically, systemically, or locally within the body of a subject. Methods for illuminating cells, tissues, and portions of subjects are known in the art.

In a related aspect, the invention provides pharmaceutical compositions include a conjugate of the invention, which may or may not be part of a nanostructure, and a pharmaceutically acceptable carrier. Suitable carriers are known in the art and include water for injection, physiological saline, and buffers.

EXAMPLES

Example 1—DNA Nanostructure

Rapid advances in structural DNA nanotechnology allow the creation of intricately shaped nanostructures that can be functionalized with a high degree of control at precise locations.[1-4] For example, DNA origami can be reliably and efficiently self-assembled by folding large, single stranded DNA with a set of specifically designed short oligonucleotide strands.[5] This technique affords a tremendous amount of control over the size and shape of the nanostructure whose designs can now be assisted by well-developed software tools.[6-8] Molecularly programed, static[9-11] or dynamic[12-14] DNA architectures hold promise for applications in areas such as cell biology,[15] NMR spectroscopy,[16] super resolution microscopy,[17] and nanotherapeutics,[18] many of which would be advanced if DNA nanostructures were capable of releasing bound cargoes at precise times.

Attempts to obtain controlled release from DNA origami nanostructures have thus far utilized two approaches through either non-covalent or covalent attachment of the cargo to origami. For example, the chemotherapy drug doxorubicin has been found to be able to non-covalently bind to DNA nanostructures through interactions with the DNA helices.[19,20] By controlling the DNA origami structure configuration, it was shown that doxorubicin release from the nanostructures could elicit a cytotoxic response in regular and drug-resistant cancer cells. Non-covalent attachment strategies however critically depend on a chemical's ability to intercalate into DNA helices. This binding mechanism cannot be generalized to most chemicals, and the binding sites within an origami cannot be easily controlled spatially. Direct covalent attachment of cargo to DNA origami nanostructures can overcome most of these limitations. To covalently attach a cargo to DNA helices, short DNA strands can be designed to protrude at specific locations on the surface of the nanostructures, which can then bind to a variety of different chemical moieties including inorganic nanoparticles,[21,22] proteins,[23] antibodies,[18] and fluorophores.[24] Placement of cleavable linkages within these DNA strands permits the release of the bound cargo in a highly controllable fashion. However, such strategies often leave a chemical remnant, the chemical group that connects the cargo to DNA strands[25] on the molecules being released, which may compromise their native biological function, limiting this approach to applications where the bioactivity of the cargo is important. Here, we demonstrate a novel and general method which releases chemically unaltered cargoes using brief pulses of light that can be broadly applied to a large variety of molecules.

We designed a novel, photolabile linker to append cargo molecules into the cavities of DNA nanostructures, so that light irradiation-induced breakage of the linker would allow the molecules to diffuse away from the protective cavity (FIGS. 1A-1E). This photolabile crosslinker possesses an o-nitrobenzyl (o-NB) motif for photo-cleavage, an azido group for attachment to alkyne functionalized oligonucleotides, and an activated carbonate group for attachment to cargo molecules possessing a free amino functional group (FIG. 1A). The linker is designed to release cargo upon photo cleavage in its original state with no chemical remnants remaining attached. Given that most peptides, proteins, and bioactive compounds contain exposed amino residues, the crosslinker design is broadly applicable to attach many molecules to DNA nanostructures, beyond the examples described here.

Figure 5:
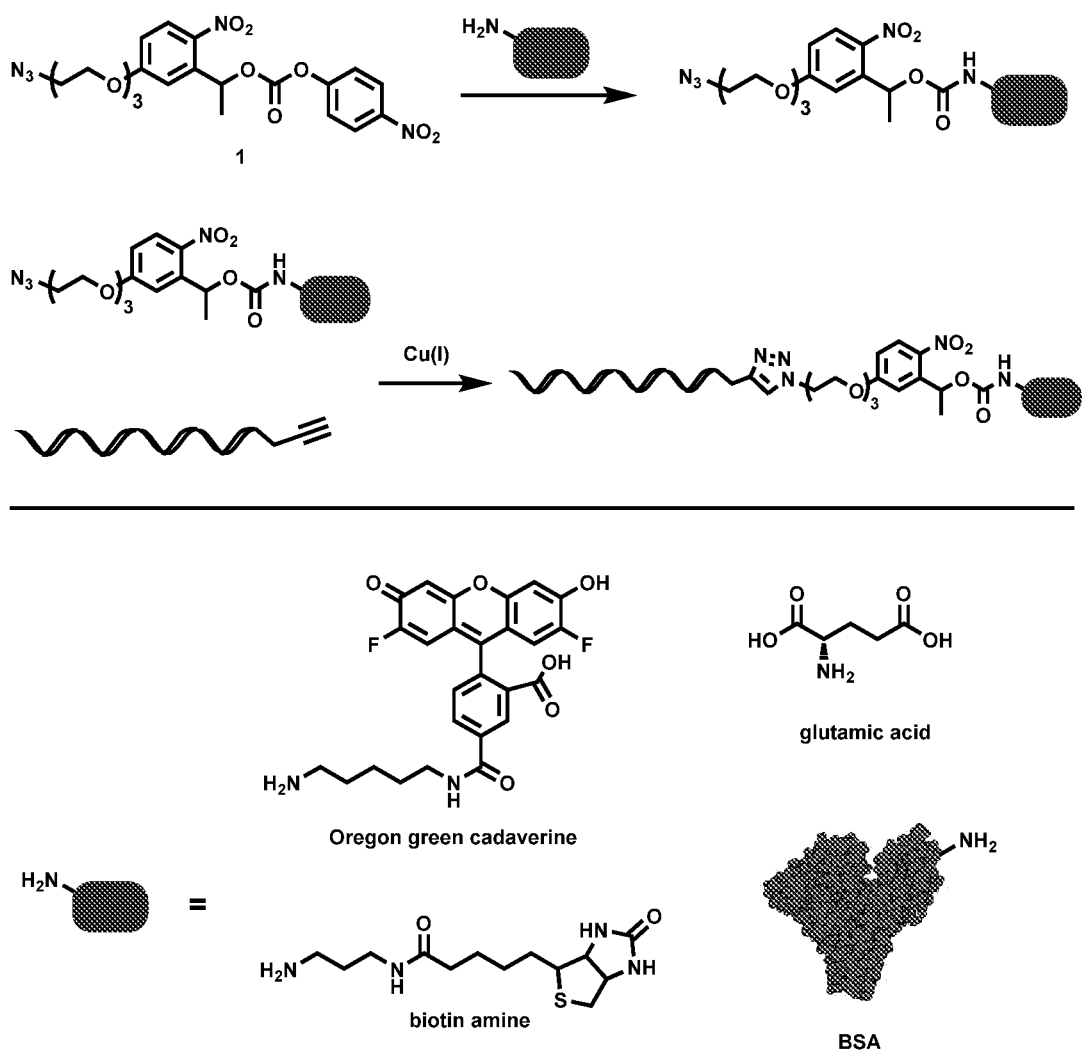
FIG. 5. General scheme for conjugation

We first synthesized this photolabile crosslinker using conventional organic synthesis techniques. Gram scale product was easily produced from inexpensive, commercially available starting materials (Scheme 1). This photolabile crosslinker was then reacted with cargo molecules including glutamate, bovine serum albumin (BSA), and biotin amine, and subsequently conjugated to oligonucleotides allowing the cargo to be incorporated into pre-assembled DNA origami through DNA base pairing (FIG. 5).

In parallel, we computationally designed a multi-layered, brick-like nanocage structure with a well-defined cavity in its center, similar to those previously reported.[6,20,26] The nanocage contains 14 addressable, single-stranded DNA extensions in its cavity, which are complementary to those presented on the activated cargo (FIG. 1B-D). Nanostructures were then self-assembled in a single step by slowly cooling a heated mixture of the DNA components. Analysis of the assembly by agarose gel electrophoresis showed a single, dominant product band that migrated faster relative to the single stranded DNA starting material (m13 DNA), consistent with that generally observed for multi-layered DNA origami structures (FIG. 1C).[9,21] Further examination with transmission electron microscopy (TEM) revealed properly assembled structures with the desired shape and a clearly visible central cavity (FIG. 1D). The short single-stranded DNA extensions however were too small to be resolved using TEM. Purification of fully formed nanostructures from excess oligonucleotides or subsequent cargo molecules was accomplished using polyethylene glycol precipitation.[27]

Fully assembled and purified DNA nanocages were then incubated with the activated cargo to attach them to the interior of the nanocage cavity. When positioned inside of the nanostructure, the cargo is protected from the exterior environment and unable to bind to its native sites of action. Release from the cage was then achieved with light irradiation which cleaved the photolabile bonds within the crosslinker (FIG. 1E).

To first validate the photo-cleavage of our crosslinkers, we used it to conjugate an oligonucleotide to the small fluorescent molecule Oregon Green cadaverine (OG). We irradiated the compound with a low-power light source over time and quantified the degree of separation of OG from the oligonucleotide using HPLC (FIG. 2A). We found that an increasing duration of light exposure led to a larger fraction of free OG dye. After 11 seconds of low-powered light irradiation, 50% of OG was released. Nearly complete cleavage was achieved after 40 seconds of exposure, consistent with the time course for the cleavage of the o-NB motif within the crosslinker.[28]

We then loaded the activated OG into the cavities of the nanostructures by incubating the OG/DNA conjugate with pre-assembled nanocages. To quantify loading efficiency, we incorporated a non-labile dye (Alexa Fluor 647N, AF647) for comparison by attaching it to a region on the nanostructure distal to the cavity (FIG. 2B). UV absorbance spectra analysis of the product showed two distinct absorption peaks centered around 500 nm and 647 nm, corresponding to the two dyes used (FIG. 2C, yellow trace). The ratio of the dye concentrations for OG versus AF647 was 7.4 to 1, suggesting that about half of the 14 DNA extensions on each cage designed to bind OG were bound, which is likely a representative loading capacity for small molecules of similar size.

To measure the efficiency of the light-induced release of OG from the nanocages, we irradiated the structures with a low powered lamp for 60 seconds, and then analyzed the absorbance spectra of the reaction solution after extensive sample dialysis of released free OG (FIG. 2B). We observed that the peak absorption at 500 nm corresponding to the photolabile OG dye was completely absent after irradiation, whereas the 647 nm absorption peak corresponding to the non-labile AF647 remained (FIG. 2C, blue trace). Together, these results demonstrate that our uncaging strategy can successfully release small molecular cargo from the DNA nanostructure upon brief low energy light irradiation.

We then explored the possibility of releasing large proteins from the nanocages, using bovine serum albumin (BSA) and streptavidin as examples that can be easily observed and analyzed using TEM. BSA was directly caged through the reaction of our crosslinker with the surface amino groups on the protein. Streptavidin was indirectly caged by attaching biotin-amine to the nanocage cavity and then subsequently mixing with the protein. TEM analysis of nanostructures at different orientations revealed clearly visible BSA and streptavidin proteins within the cavity of the DNA cage (FIGS. 3Ai-3Biii). None were seen tethered to the cage exterior. The number of DNA nanostructures with and without proteins was determined via particle counting of TEM images, and a loading efficiency of 93% for BSA and 71% for streptavidin was observed. After low power light irradiation for 60 seconds, we found only 19% of nanocages contained BSA, and 9% cages contained streptavidin, which corresponds to uncaging efficiencies of 79% for BSA and 87% for streptavidin. Together, these results demonstrate that full sized proteins can be effectively encapsulated and uncaged with high efficiency.

To demonstrate that molecules released from the DNA nanocages retain their bioactivity, we tested uncaging of the small molecule glutamic acid, an excitatory neurotransmitter which has been shown to be successfully uncaged in numerous instances (FIG. 4A).[29,31] The bioactivity of the released glutamate from the nanocages was measured by glutamate mediated calcium changes in cultured neurons using real-time fluorescence imaging. Primary hippocampal neuron cultures were incubated with the intracellular calcium dye Fluo-4 and the glutamate-containing DNA nanocages. Before light illumination, little basal calcium activity was observed in the 9 days old cultures, consistent with the general activity patterns observed in neuron cultures of this age (FIGS. 4B and 4C).[32] Immediately following a 1 ms light pulse illumination (240-400 nm), we observed an increase in intracellular calcium levels in 16.22% (N=185 neurons, analyzed in 2 tests) (FIG. 4C). Activated cells exhibited heterogeneity in response amplitude with activation onsets ranged from 509 ms to 18.19 s after the light pulse, which could be due to difference in diffusion time from the releasing site to the cell surface, the concentration of released glutamic acid on a given cell, and intrinsic variability of cellular calcium responses (FIG. 4D). The fact that light irradiation was delivered for 1 ms suggests that uncaging can be performed with millisecond temporal resolution. In the absence of the DNA nanocages, no cells exhibited a change in calcium levels upon light illumination (N=124 neurons, analyzed in 2 tests) (FIG. 4B). Together, these results demonstrate that DNA nanocages can be used to release functional bioactive molecules with millisecond temporal precision.

In conclusion, we describe a novel strategy to encapsulate bioactive molecules inside DNA nanostructures and release them using pulses of light. This strategy is realized through tagging DNA origami with a novel photolabile crosslinker that can be broadly used to encapsulate a large variety of molecules. With this crosslinker, a single, general chemical reaction scheme can be used to attach chemicals of interest to DNA origami through reacting with amino groups which are present on many biologically relevant compounds. This technique allows the release of cargo in its unaltered, bioactive state in contrast to existing labile conjugation chemistries, which often leave behind a chemical remnant that may interfere with the natural bioactivity of the cargo. This strategy was shown to be effective for a range of molecular sizes, from small molecules to full-sized proteins. Our nanocage design offers a high degree of addressability and customization, and versions could be created that accommodate a larger variety of cargo molecules or cocktails of molecules in precise stoichiometries by controlling the shape and dimensions of the nanostructures as well as the sequences of the strands protruding from the cavity. While light controlled uncaging techniques have been successful in releasing small molecules that rely on small, photochemical blocking chemical groups, our nanocaging platform could be easily designed to release many previously un-cagable compounds and accelerate progress in understanding chemical receptor binding or controlled release of therapeutics.

REFERENCES (1) Seeman, N. C. *Nature* 2003, 421, 427.
(2) Seeman, N. C. *Ann. Rev. Biochem.* 2010, 79, 65.
(3) Zhang, F.; Nangreave, J.; Liu, Y.; Yan, H. *J. Am. Chem. Soc.* 2014, 136, 11198.
(4) Jones, M. R.; Seeman, N. C.; Mirkin, C. A. *Science* 2015, 347.
(5) Rothemund, P. W. K. *Nature* 2006, 440, 297.
(6) Douglas, S. M.; Marblestone, A. H.; Teerapittayanon, S.; Vazquez, A.; Church, G. M.; Shih, W. M. *Nucleic Acids Res.* 2009, 37, 5001.
(7) Kim, D.-N.; Kilchherr, F.; Dietz, H.; Bathe, M. *Nucleic Acids Res.* 2012, 40, 2862.
(8) Pan, K.; Kim, D.-N.; Zhang, F.; Adendorff, M. R.; Yan, H.; Bathe, M. *Nat. Commun.* 2014, 5.
(9) Douglas, S. M.; Dietz, H.; Liedl, T.; Hogberg, B.; Graf, F.; Shih, W. M. *Nature* 2009, 459, 414.
(10) Han, D.; Pal, S.; Yang, Y.; Jiang, S.; Nangreave, J.; Liu, Y.; Yan, H. *Science* 2013, 339, 1412.
(11) Benson, E.; Mohammed, A.; Gardell, J.; Masich, S.; Czeizler, E.; Orponen, P.; Hogberg, B. *Nature* 2015, 523, 441.
(12) Bath, J.; Turberfield, A. J. *Nat. Nano.* 2007, 2, 275.
(13) Kohman, R. E.; Han, X. *Chem. Commun.* 2015, 51, 5747.
(14) Gerling, T.; Wagenbauer, K. F.; Neuner, A. M.; Dietz, H. *Science* 2015, 347, 1446.
(15) Shaw, A.; Lundin, V.; Petrova, E.; Fordos, F.; Benson, E.; AI-Amin, A.; Herland, A.; Blokzijl, A.; Hogberg, B.; Teixeira, A. I. *Nat. Meth.* 2014, 11, 841.
(16) Douglas, S. M.; Chou, J. J.; Shih, W. M. *Proc. Natl. Acad. Sci.* 2007, 104, 6644.
(17) Jungmann, R.; Avendano, M. S.; Woehrstein, J. B.; Dai, M.; Shih, W. M.; Yin, P. *Nat. Meth.* 2014, 11, 313.
(18) Douglas, S. M.; Bachelet, I.; Church, G. M. *Science* 2012, 335, 831.
(19) Jiang, Q.; Song, C.; Nangreave, J.; Liu, X.; Lin, L.; Qiu, D.; Wang, Z.-G.; Zou, G.; Liang, X.; Yan, H.; Ding, B. *J. Am. Chem. Soc.* 2012, 134, 13396.
(20) Zhao, Y.-X.; Shaw, A.; Zeng, X.; Benson, E.; Nyström, A. M.; Högberg, B. *ACS Nano* 2012, 6, 8684.
(21) Zhao, Z.; Jacovetty, E. L.; Liu, Y.; Yan, H. *Angew. Chem. Int. Ed.* 2011, 50, 2041.
(22) Schreiber, R.; Do, J.; Roller, E.-M.; Zhang, T.; Schuller, V. J.; Nickels, P. C.; Feldmann, J.; Liedl, T. *Nat. Nano* 2014, 9, 74.
(23) Rinker, S.; Ke, Y.; Liu, Y.; Chhabra, R.; Yan, H. *Nat. Nano* 2008, 3, 418.
(24) Dutta, P. K.; Varghese, R.; Nangreave, J.; Lin, S.; Yan, H.; Liu, Y. *J. Am. Chem. Soc.* 2011, 133, 11985.

(25) Voigt, N. V.; Torring, T.; Rotaru, A.; Jacobsen, M. F.; Ravnsbaek, J. B.; Subramani, R.; Mamdouh, W.; Kjems, J.; Mokhir, A.; Besenbacher, F.; Gothelf, K. V. *Nat. Nano* 2010, 5, 200.
(26) Sun, W.; Boulais, E.; Hakobyan, Y.; Wang, W. L.; Guan, A.; Bathe, M.; Yin, P. *Science* 2014, 346.
(27) Stahl, E.; Martin, T. G.; Praetorius, F.; Dietz, H. *Angew. Chem. Int. Ed.* 2014, 53, 12735.
(28) Holmes, C. P. *J. Org. Chem.* 1997, 62, 2370.
(29) Matsuzaki, M.; Ellis-Davies, G. C. R.; Nemoto, T.; Miyashita, Y.; Iino, M.; Kasai, H. *Nat. Neuro.* 2001, 4, 1086.
(30) Fino, E.; Araya, R.; Peterka, D. S.; Salierno, M.; Etchenique, R.; Yuste, R. *Frontiers in Neural Circuits* 2009, 3.
(31) Olson, J. P.; Kwon, H.-B.; Takasaki, K. T.; Chiu, C. Q.; Higley, M. J.; Sabatini, B. L.; Ellis-Davies, G. C. R. *J. Am. Chem. Soc.* 2013, 135, 5954.
(32) Soriano, J.; Rodriguez Martinez, M.; Tlusty, T.; Moses, E. *Proc. Natl. Acad. Sci.* 2008, 105, 13758.

EXPERIMENTAL SECTION

Crosslinker 1 Synthesis (Scheme 1):

Reactions were monitored by TLC using glass-backed silica gel 60 F254 plates. Flash chromatography was performed in a quartz column with a fluorescent indicator (green 254 nm) added to the silica gel. TLC bands were visualized by UV. Solvent ratios used as eluants are reported in v/v. The purity of the final products was obtained through $^1$H NMR and $^{13}$C NMR.

$^1$H NMR data were obtained on a 500 MHz Varian VMNRS spectrophotometer at the Chemical Instrumentation Center at Boston University. Chemical shifts are reported in parts per million (ppm) and coupling constants were reported in Hertz (Hz). $^1$H NMR spectra obtained in CDCl$_3$ were referenced to 7.26 ppm and those obtained in DMSO-d6 were referenced to 2.50 ppm. ESIMS data were collected on an Agilent Single-Quad LC/MSD VL instrument at the Chemical Instrumentation Center at Boston University.

The following compounds were synthesized according to literature procedures: 5-hydroxy-2-nitroacetophenone (S1)[1] and ethylene glycol 2-azidoethyl ether tosylate (S2)[2].

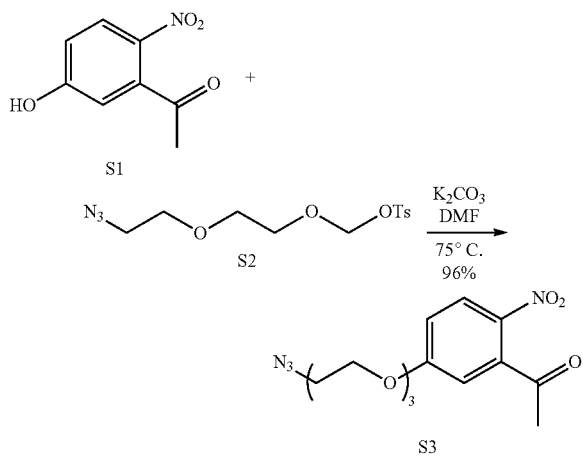

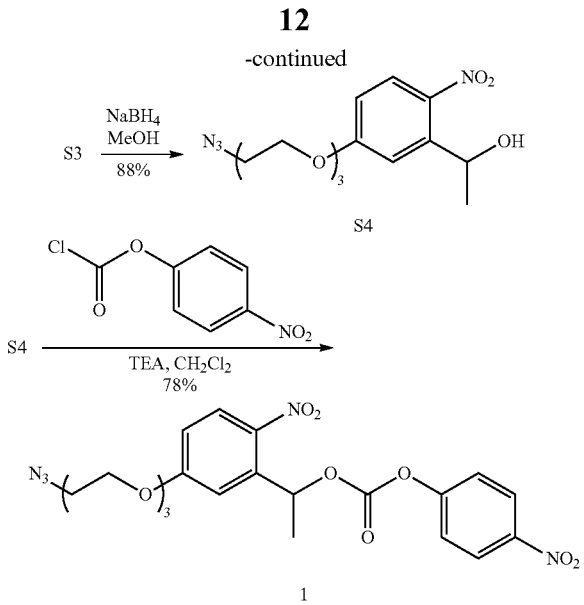

1-(5-(2-(2-(2-azidoethoxy)ethoxy)ethoxy)-2-nitrophenyl)ethan-1-one (S3)

To a solution of 5-hydroxy-2-nitroacetophenone (2.46 g, 13.6 mmol) and ethylene glycol 2-azidoethyl ether tosylate (4.36 g, 13.2 mmol) in DMF (15 mL) was added potassium carbonate (3.77 g, 27.3 mmol), and the suspension was heated to 75'C. After 18 hours, the solution was concentrated in vacuo and partitioned between CH$_2$Cl$_2$ (40 mL) and NaHCO$_3$ (20 mL). The organic layer was washed with NaHCO$_3$ (3×10 mL), dried over Na$_2$SO$_4$, filtered, and concentrated in vacuo to produce 4.30 g (96% crude) of S3 as a dark brown oil that was taken on without further purification: $^1$H NMR (500 MHz, DMSO-d6) δ 8.14 (d, J=9.1 Hz, 1H), 7.21 (dd, J=2.8 Hz, 9.1 Hz, 1H), 7.19 (d, J=2.8 Hz, 1H), 4.29 (m, 2H), 3.79 (m, 2H), 3.59 (m, 6H), 3.38 (m, 2H), 2.53 (s, 3H).

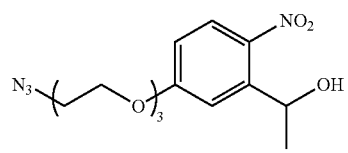

1-(5-(2-(2-(2-azidoethoxy)ethoxy)ethoxy)-2-nitrophenyl)ethan-1-ol (S4)

To a solution of S3 (4.12 g, 12.2 mmol) in MeOH (30 mL) stirring in an ice bath was added sodium borohydride (723 mg, 18.7 mmol) in portions. After 2 hours, the solution was concentrated in vacuo and partitioned between CH$_2$Cl$_2$ (30 mL) and brine (20 mL). The organic layer was washed with NaHCO$_3$ (3×10 mL), dried over Na$_2$SO$_4$, filtered, concentrated in vacuo, and purified via flash chromatography (2:1 ethyl acetate:petroleum ether) to afford 3.63 g (88%) of S4 as a yellow oil: $^1$H NMR (500 MHz, CDCl$_3$) δ 8.03 (d, J=9.1 Hz, 1H), 7.37 (d, J=2.8 Hz, 1H), 6.88 (dd, J=2.8 Hz, 9.1 Hz, 1H), 5.55 (dq, J=4.0 Hz, 6.3 Hz, 1H), 4.24 (m, 2H), 3.90 (m, 2H), 3.74 (m, 2H), 3.68 (m, 4H), 3.38 (m, 2H), 2.40 (d, J=4.0 Hz, 1H), 1.54 (d, J=6.3 Hz, 3H).

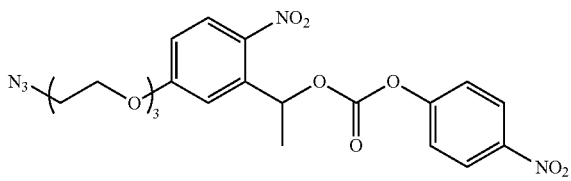

Crosslinker (1).

To a solution of S4 (1.88 g, 5.51 mmol) and 4-nitrophenyl chloroformate (1.65 g, 7.86 mmol) in CH$_2$Cl$_2$ (21 mL) was added triethylamine (1.50 mL, 10.8 mmol). After stirring for 24 hours, CH$_2$Cl$_2$ (30 mL) was added and the solution was washed with NaHCO$_3$ (20 mL), dried over Na$_2$SO$_4$, filtered, concentrated in vacuo, and purified via flash chromatography (gradient from 1:3 to 2:3 ethyl acetate:petroleum ether) to afford 2.16 g (78%) of S4 as a tan oil: $^1$H NMR (500 MHz, CDCl$_3$) δ 8.26 (d, J=9.3 Hz, 2H), 8.12 (d, J=9.1 Hz, 1H), 7.37 (d, J=9.3 Hz, 2H), 7.24 (d, J=2.7 Hz, 1H), 6.95 (dd, J=2.7 Hz, 9.1 Hz, 1H), 6.53 (quart, J=6.3 Hz, 1H), 4.25 (m, 2H), 3.93 (m, 2H), 3.76 (m, 2H), 3.69 (m, 4H), 3.39 (m, 2H), 1.76 (d, J=6.2 Hz, 3H).

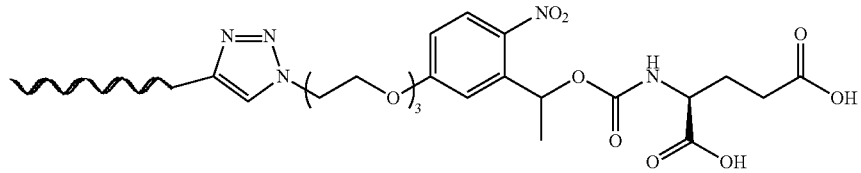

Glutamic Acid Conjugate.

To a solution of crosslinker 1 (322 mg, 637 μmol) and L-glutamic acid di-tert-butyl ester hydrochloride (217 mg, 734 μmol) in CH$_2$Cl$_2$ (6 mL) was added triethylamine (570 μL, 4.09 mmol). After stirring for 48 hours, CH$_2$Cl$_2$ (25 mL) was added and the solution was washed with NaHCO$_3$ (2×15 mL). The combined aqueous layers were washed with CH$_2$Cl$_2$ (2×10 mL). The combined organic layers were dried over Na$_2$SO$_4$, filtered, concentrated in vacuo, and purified via flash chromatography (1:2 ethyl acetate:petroleum ether) to afford 383 mg of a yellow oil. To a solution of this intermediate in CH$_2$Cl$_2$ (5 mL) was added trifluoroacetic acid (700 μL, 9.15 mmol). The solution was concentrated in vacuo and purified via flash chromatography (5% MeOH in CH$_2$Cl$_2$) to afford 152 mg (47% over 2 steps) of product: $^1$H NMR (500 MHz, DMSO-d6) δ 8.1 (dd, J=2.0 Hz, J=9.0 Hz, 1H), 7.8 (d, J=8 Hz, 1H), 7.2 (dd, J=2.8 Hz, J=17.3 Hz, 1H), 7.1 (m, 1H), 6.1 (m, 1H), 4.3 (m, 2H), 3.9 (m, 1H), 3.8 (quart, J=3.2 Hz, 2H), 3.6 (m, 4H), 3.4 (m, 2H), 2.3-2.2 (m, 2H), 2.0-1.7 (m, 2H), 1.5 (t, J=6.8 Hz, 2H), 1.4 (d, J=8.5 Hz, 3H). ESI-LRMS m/z 512.1 (M−) Product molecular weight=513.46. Azido intermediate was reacted with the oligo-alkyne using the general bioconjugate protocol and purified via HPLC to afford a solution of the product.

General Bioconjugate Protocol (FIG. 5):

Bioactive, amino-group containing compounds were first reacted in slight excess with Crosslinker 1 in organic solvents such as methylene chloride or dimethylformamide and trimethylamine. In cases where the starting material was insoluble, a dimethylsulfoxide/aqueous buffer mixture was used.

Carbonate intermediates were subsequently reacted with an alkyne functionalized oligonucleotide via the copper catalyzed azide alkyne cycloaddition (CuAAC) reaction using published procedures.[3] In brief, equal volumes of alkyne functionalized oligonucleotide (410 uM in PBS) and activated carbonate (1 mM in DMSO) were mixed. A solution of copper sulfate (10 equivalents, 20 mM in water) and tris(3-hydroxypropyltriazoylmethyl)amine (THPTA) (50 equivalents, 50 mM in water) were separately mixed together and added to the reaction mixture. Lastly, a solution of sodium ascorbate (120 equivalents, 100 mM) was added and the reaction was stirred overnight. The reaction was subsequently purified via HPLC (TSKgel OligoDNA RP column, Tosoh Bioscience) using a gradient from 1:19 to 3:2 acetonitrile: 100 mM ammonium acetate over 30 minutes.

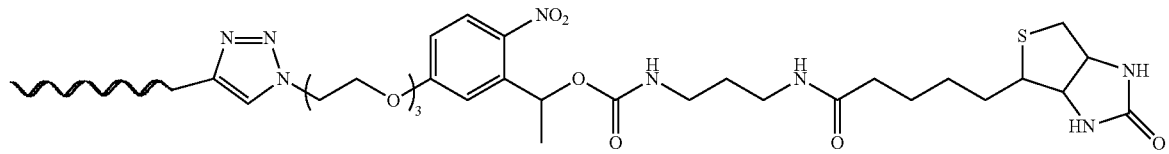

Biotin Bioconjugate.

To a solution of crosslinker 1 (103 mg, 204 μmol) and biotin-amine (100 mg, 234 μmol) in CH$_2$Cl$_2$ (1 mL) and DMF (1 mL) was added triethylamine (150 μL, 1.08 mmol). After stirring for 2 hours the solvent was removed with a stream of air. CH$_2$Cl$_2$ (25 mL) was added and the solution was washed with NaHCO$_3$ (15 mL). The aqueous layer was washed with CH$_2$Cl$_2$ (10 mL). The combined organic layers were dried over Na$_2$SO$_4$, filtered, concentrated in vacuo, and purified via flash chromatography (gradient 2% to 10% MeOH in CH$_2$Cl$_2$) to afford 109 mg (80%) of a solid: $^1$H NMR (500 MHz, DMSO-d6) δ 8.1 (d, J=9.0 Hz, 1H), 7.7 (t, J=5.8 Hz, 1H), 7.4 (t, J=5.8 Hz, 1H), 7.1 (m, 2H), 6.4 (s, 1H), 6.3 (s, 1H), 6.1 (quart, J=6.5 Hz, 1H), 4.2 (m, 3H), 4.21 (m, 1H), 3.8 (t, J=4.5 Hz, 2H), 3.6 (m, 4H), 3.4 (t, J=5.0 Hz, 2H), 3.1 (m, 2H), 3.0 (m, 2H), 3.0-2.8 (m, 2H), 2.6 (d, J=12.5 Hz, 1H), 2.0 (t, J=7.5 Hz, 2H), 1.5 (m, 5H), 1.6-1.2 (m, 8H). Azido intermediate (128 µL, 2 mM in DMSO, 256 nmol) was reacted with the oligo-alkyne (120 µL, 410 µM in 1×PBS, 49.2 nmol) using the general bioconjugate protocol. The product was isolated by ethanol precipitation and purified via HPLC to afford 11.3 nmol as a 100 µL, 113 µM solution of the product.

the cavity interior) and incubated overnight at 40° C. and subsequently purified by at least two rounds of PEG precipitation[6].

Gel Electrophoreals.

Reaction solutions were electrophoresed on 1.5% agarose gels containing 0.5×TBE, supplemented with 10 mM $MgCl_2$. DNA dye SybrSafe was mixed with gel solutions

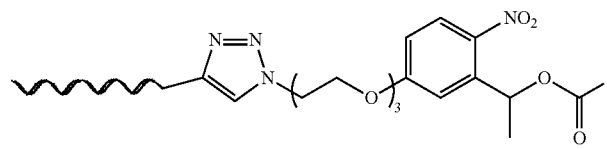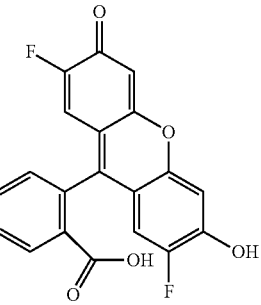

Oregon Green Conjugate.

To a solution of crosslinker 1 (1.25 mg, 2.52 µmol) and Oregon Green cadaverine (1.21 mg, 2.39 µmol) in DMF (300 µL) and water (20 µL) was added triethylamine (20 µL, C). After stirring overnight the solution was purified via HPLC to afford 2.39 mg an orange solid: ESI-LRMS m/z 863.2 (M+) Product molecular weight=862.80. Azido intermediate (150 µL, 1 mM in DMSO, 150 nmol) was reacted with the oligo-alkyne (150 µL, 410 µM in 1×PBS, 61.5 nmol) using the general bioconjugate protocol and purified via HPLC to afford 38 nmol as a 200 µL, 190 µM solution (62%) of the product.

BSA Conjugate.

A solution of BSA (200 µL, 500 µM in 1×PBS, 100 nmol) and crosslinker 1 (20 µL, 5 mM in DMSO, 1000 nmol) in 80 µL DMSO was mixed overnight. The reaction was centrifuged at 17000 rcf for 5 minutes to pellet insoluble materials. The supernatant was dialyzed in 1×PBS against a 25 kDa cutoff to afford 300 µL (333 µM) of product. Azido intermediate (50 µL, 333 µM in PBS, 16.7 nmol) was reacted with the oligo-alkyne (200 µL, 410 µM in 1×PBS, 82 nmol) using the general bioconjugate protocol and purified using Amicon spin filters (3 spins with 30 kDa cutoff tube and 3 spins with 50 kDa cutoff tube) against buffer (5 mM Tris, 1 mM EDTA, and 16 mM $MgCl_2$) to produce 50 uL of product solution.

Design and Assembly of DNA Nanostructures.

Figure 7:
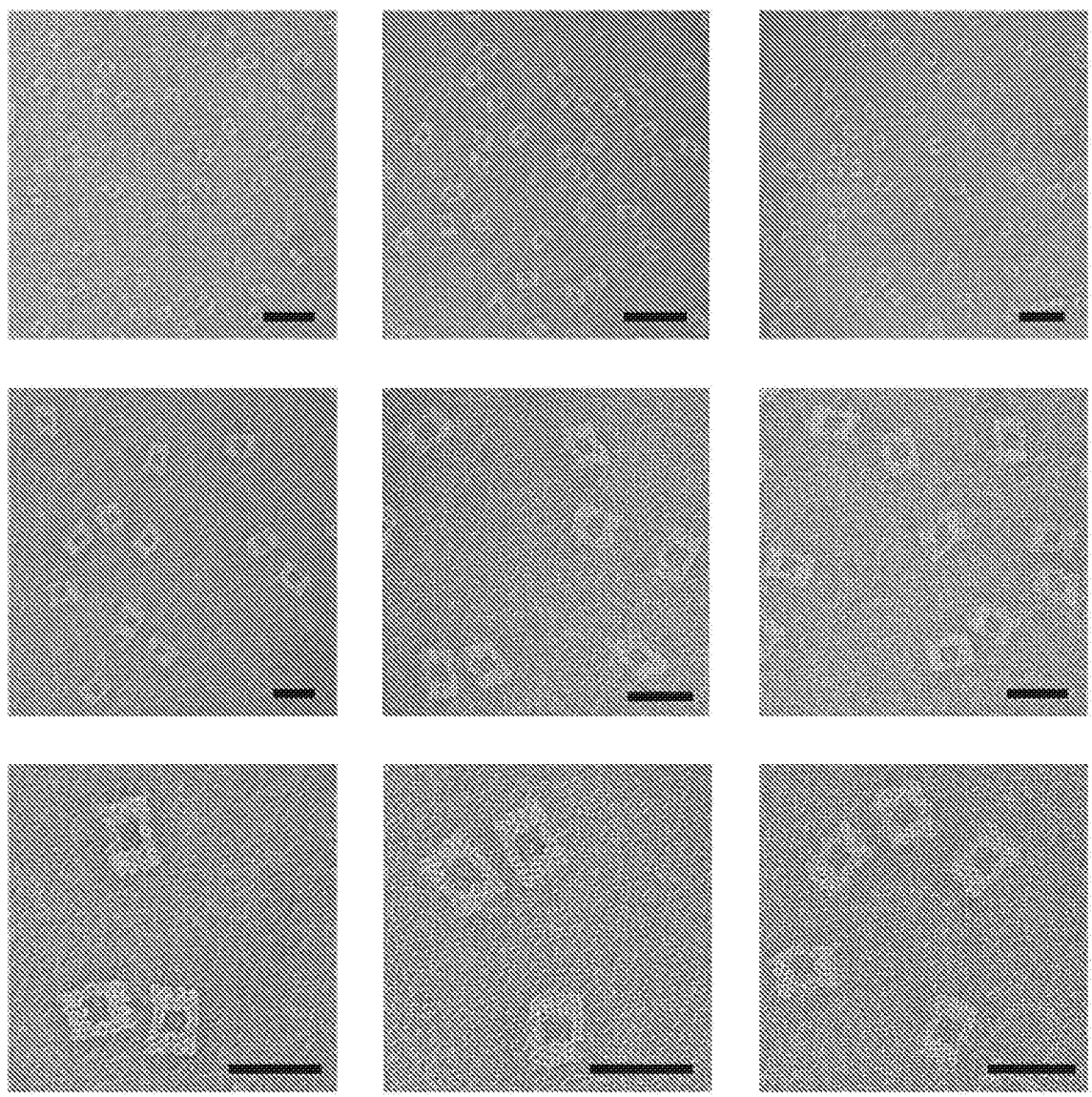
FIG. 7. TEM images of unmodified DNA nanocage. Scale bars equal 100 nm (top three images) and 50 nm (remaining six images).

Nanostructures were designed using caDNAno.[4] Single stranded M13mp18 bacteriophage DNA was prepared as described previously.[5] All oligonucleotides were purchased from Integrated DNA Technologies (IDT) and used with no additional purification. Creation of nanostructures was performed by first heating a solution containing a final concentration of 40 nM m13 scaffold DNA and 200 nM of each staple in a folding buffer containing 5 mM Tris, 1 mM EDTA, and 20 mM $MgCl_2$ to 80% C, followed by cooling from 80° C. to 60° C. over 80 minutes, and then from 60% C to 24° C. over 48 hours. Removal of excess staple strands was accomplished by three rounds of precipitation with polyethylene glycol solutions.[6] Pellets were re-dissolved in 5 mM Tris, 1 mM EDTA, and 16 mM $MgCl_2$. FIG. 7 shows a TEM image of unmodified nanocages.

Cavity Functionalization.

Nanostructures were mixed with 70 equivalents of oligo bioconjugates (5 equivalents per handle, with 14 handles in before loading onto the gel. The gel box was submerged in an ice water bath to prevent excessive heating.

TEM Sample Preparation and Imaging.

TEM samples were prepared by placing 3 µL of sample solution onto a carbon coated grid (FCF400-Cu, Electron Microscopy Sciences) which was previously charged using a plasma etcher (30 seconds of irradiation). After 2 minutes, the solution was wicked away from the grid with filter paper (Whatman 50 hardened). The grid was immediately treated with stain for 30 seconds and excess solution was wicked away. The remaining solution on the grid was evaporated at room temperate prior to imaging. TEM images were acquired with an FEI Tecnai Spirit Transmission Electron Microscope operated at 80 kV. Saturated uranyl formate (in $ddH_2O$ prepared freshly before usage) was used for protein caging experiments and 2% uranyl acetate (diluted with $ddH_2O$ from 4%, Electron Microscopy Sciences) was used for all other samples.

Kinetics of o-NB Cleavage.

Figure 6:
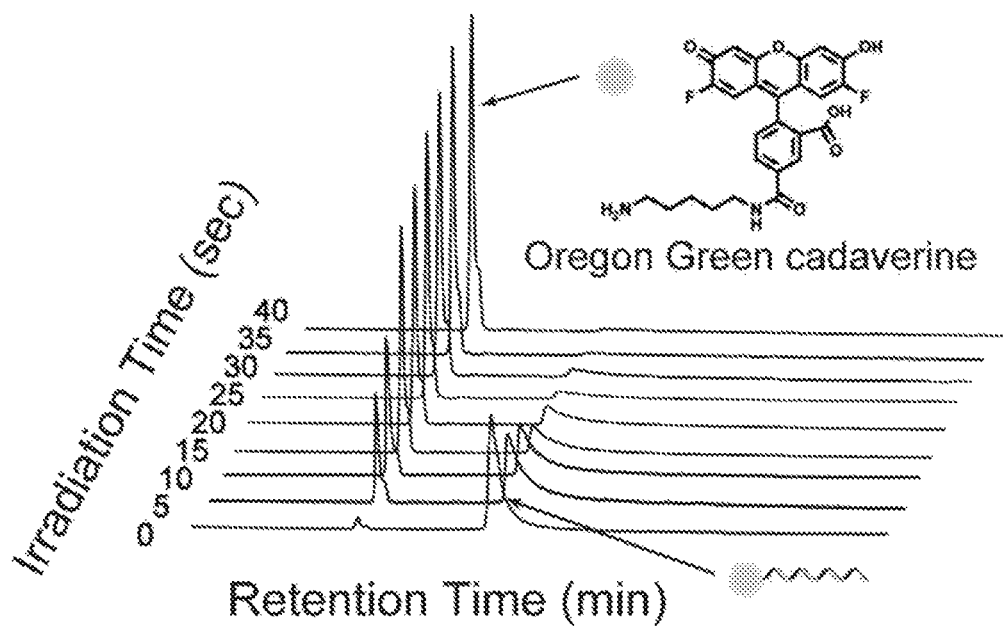
FIG. 6. HPLC traces of Oregon Green cadaverine photolysis experiment. Increased irradiation duration results in an increase in the cleavage of Oregon Green/oligonucleotides conjugate. A wavelength of 490 nm was used to monitor traces.

Samples of the Oregon Green cadaverine oligonucleotide bioconjugate were irradiated with a handheld UV lamp (UVM-57, 6 W, 302 nm) for varying lengths of time and analyzed using HPLC (TSKgel OligoDNA RP column, Tosoh Bioscience) using a gradient from 1:19 to 3:2 acetonitrile:100 mM ammonium acetate over 30 minutes. Irradiation durations used were 5, 10, 15, 20, 25, 30, 35, 40, and 60 seconds. A UV detector monitoring at 490 nm was used to collect traces containing Oregon Green. The degree of o-NB cleavage was obtained by comparing the areas under the peaks corresponding to the Oregon Green-oligo conjugate starting material with the released Oregon Green cadaverine (FIG. 6).

2 Dye Labeling Experiment.

The general cavity functionalization protocol was followed but with two different oligos. 5 oligos per binding site were used. The cavity contained 14 binding sites for the activated Oregon green oligo, whereas 1 binding site on the unfolded loop was available for the Alexa Fluor 647 oligo. Reactions were incubated overnight at 40° C. and subsequently purified by at least two rounds of PEG precipitation[6]. The final solution was analyzed using the UV setting of a Nanodrop 2000. The ratio of the dyes was obtained by comparing the concentrations of each dye in solution as calculated with Beer's law.

Oregon Green Cadaverine Uncaging.

25 μL 2 dye labeled nanostructures was irradiated with a handheld UV lamp (UVM-57, 6 W, 302 nm) for 60 seconds. The solution was placed in half of a microdialysis chamber and dialyzed against 2 μL of buffer (5 mM Tris, 1 mM EDTA, and 16 mM $MgCl_2$) overnight. The resulting solution was analyzed using the UV setting of a Nanodrop 2000.

Protein Uncaging.

Figure 8:
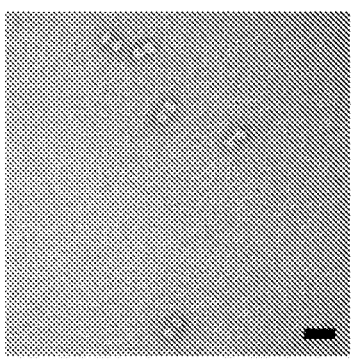
FIG. 8. TEM images of streptavidin containing DNA nanocages before (top) and after (bottom) light irradiation. Scale bars equal 50 nm.
Figure 8:
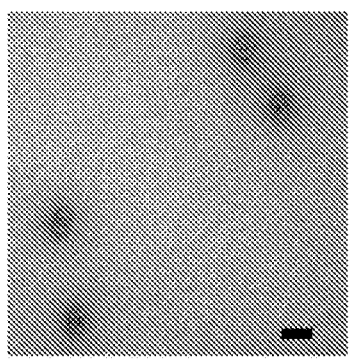
Figure 8:
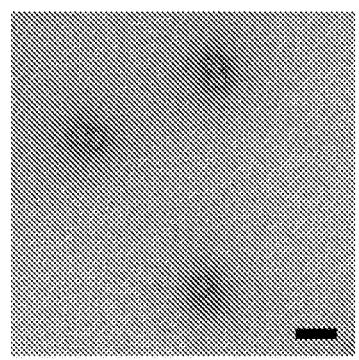
Figure 8:
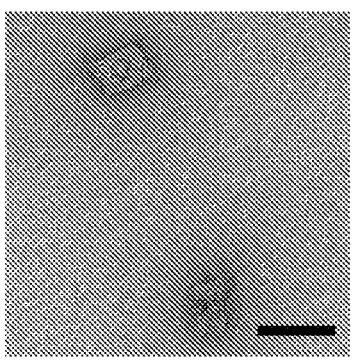
Figure 8:
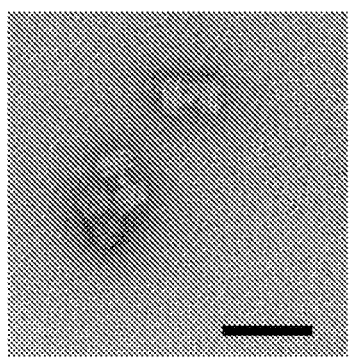
Figure 8:
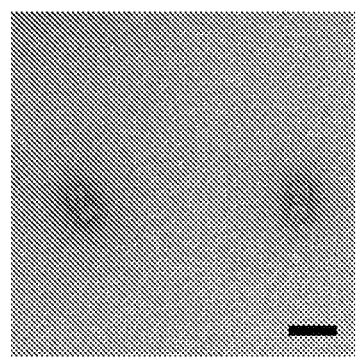
Figure 8:
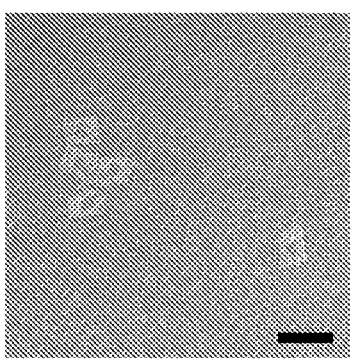
Figure 8:
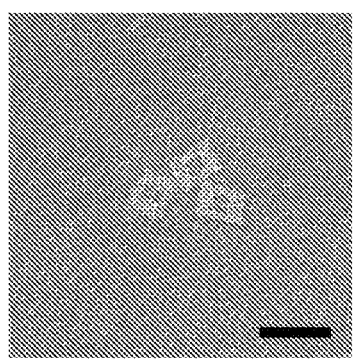
Figure 8:
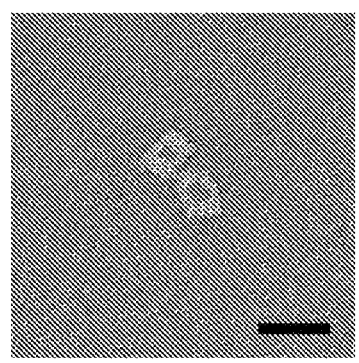
Figure 8:
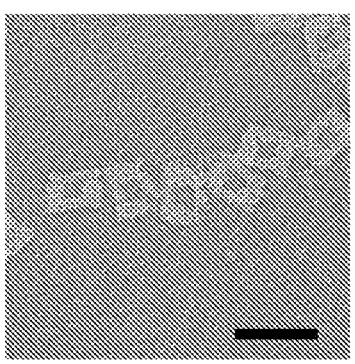
Figure 8:
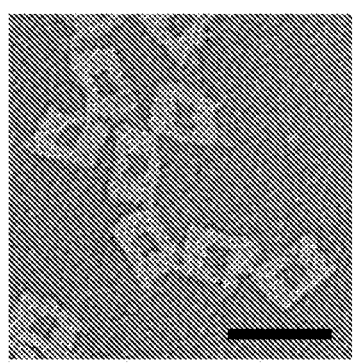
Figure 8:
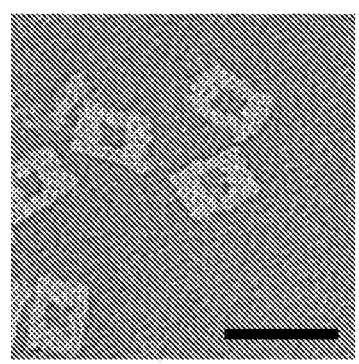
Figure 9:
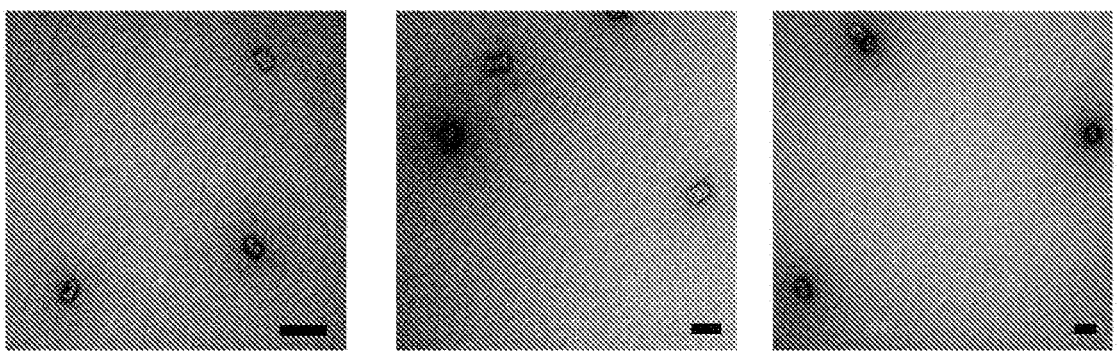
FIG. 9. TEM images of bovine serum albumin containing DNA nanocages before (top) and after (bottom) light irradiation. Scale bars equal 50 nm.
Figure 9:
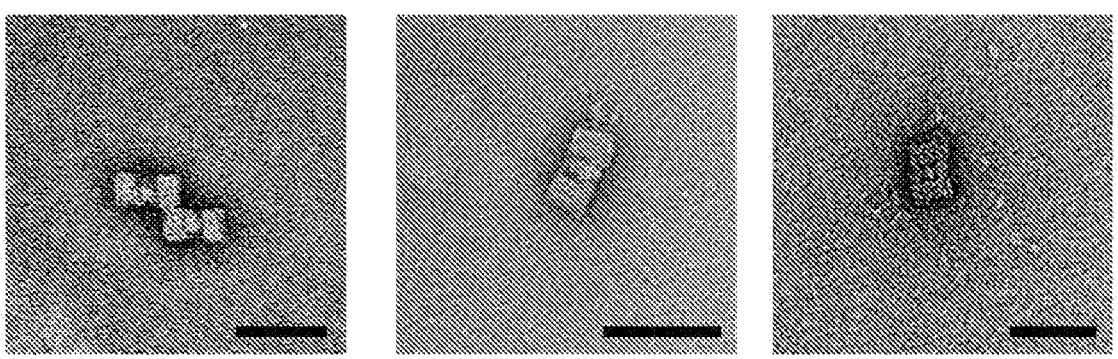
Figure 9:
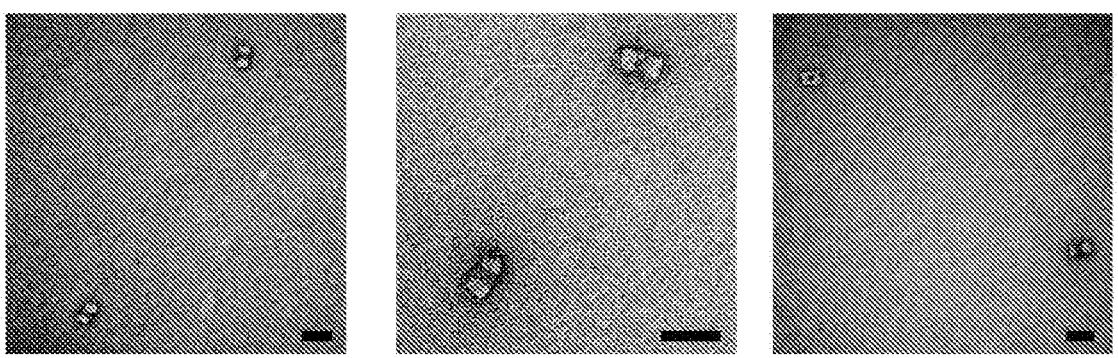
Figure 9:
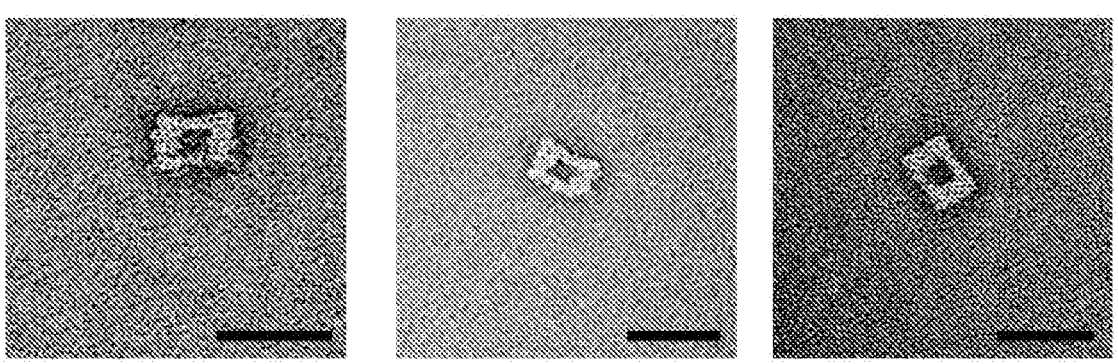

Protein containing nanocages were created following the general cavity functionalization protocol. 5 equivalents per oligo handle were used. For BSA encapsulation, the BSA/oligo bioconjugate was used. For streptavidin, the nanocage was first modified with the biotin-amine/oligo bioconjugate and subsequently with streptavidin (5 equivalents per oligo handle). Each round of modification was purified using two rounds of PEG precipitation[6]. Uncaging experiments were performed by irradiating a PCR tube containing 5 uL of a 0.5 nM solution of protein-containing nanocage for 60 seconds with a handheld UV lamp (UVM-57, 6 W, 302 nm). Samples were heated at 40° C. for 30 seconds and then imaged by TEM (FIGS. 8 and 0). The extent of uncaging was analyzed using particle counting of the TEM images. The entirety of each TEM image was analyzed to avoid bias.

Glutamate Uncaging.

Glutamate containing nanocages were created following the general cavity functionalization protocol. 5 equivalents of activated glutamate/oligo handle were used. Reactions were incubated overnight at 40° C. and subsequently purified by three rounds of PEG precipitation[6]. For cell testing, the structures were PEG precipitated and dissolved in a modified Tyrode buffer (25 mM HEPES, 119 mM NaCl, 5 mM KCl, 2 mM $CaCl_2$, 10 mM $MgCl_2$, pH 7.4), at a final concentration of 180 nM. 9 days old primary rat hippocampal neurons were prepared on 12 mm diameter glass coverslides. The calcium dye Fluo-4 AM (life technologies) was dissolved in DMSO to yield a stock concentration of 2.3 mM. Neurons were loaded for 30 min in Fluo-4 AM at 2.3 uM, diluted in the modified Tyrode buffer at room temperature. Neurons were then rinsed three times with Tyrode buffer, and incubated at 37 C for another 30 min to allow complete de-esterification of intracellular AM esters. Glass coverslides were fractured into smaller pieces (approximately 1 $mm^2$) with a pointed tungsten-carbide glass cutter to limit the use of nanocage reagents. The buffer was wicked off the surface of the fractured glass and replaced with 2 uL glutamate containing nanostructures in Tyrode. Neurons were then placed under a custom microscope with a 10× objective, equipped with a 5 W LED (LZ1-00B200, 460 nm; LedEngin, San Jose Calif.) for excitation, an excitation filter (HQ 470/50), a dichroic mirror (FF506-Di02), an emission filter (FF01-536/40), and imaged with a Hamamatsu camera (C11440-42U) at 20 Hzn After baseline activity was collected for 5 s, the flash lamp (JML-C2, Rapp OptoElectronic GmbH, Hamburg, Germany) was triggered to deliver a light pulse for 1 ms at 240-400 nm, and the calcium activities of neurons were measured for another 25 s.

Calcium Signal Processing.

All analysis was conducted with MATLAB (MathWorks, Massachusetts, US). Individual neurons were manually identified, and the mean fluorescence intensity averaged for all pixels within each neuron was then further processed to represent individual neuron calcium changes. Due to the saturation effects of the high intensity uncaging flash light that lasted for 6 frames (300 ms) following the light illumination, the fluorescence intensities of these 6 frames were removed and replaced by a linear fit connecting the end values that were not affected by the flash. The fluorescence of each neuron was first baseline subtracted using its linear fit for the 5 second baseline period, and then normalized by the standard deviation of the baseline and smoothed using a built-in function, Smooth, with a moving average filter with the span of 25 frames. The temporal derivative of the signal was calculated and smoothed using the moving average filter with the span of 6 frames. To screen for activated cells, we first calculated the root mean squared error (RMSE) for each 5 second intervals throughout the 30 second recording sessions, and thus 6 RMSE values were calculated. We then used the maximum RMSE of these 6 values to represent the RMSE of each neuron, and obtained the 95% confidence interval of the RMSE for the control group. We then calculated the threshold value for the instantaneous temporal derivative that would correspond to the 95% confidence interval of the RMSE. Cells were deemed as activated when their temporal derivative exceeds the threshold. To determine the onset of calcium responses, we calculated the z score of the fluorescence trace of the activated cells. Onset threshold were set as the first time point of 10 consecutive points in which the temporal derivative values had a z score bigger than 3.

Staple List:

Center staples-those which do not come in contact with the edges of the nanostructure

| SEQ ID NO | SEQUENCE |
|---|---|
| 1. | GGATTAGCAATATAAAAAGCG |
| 2. | AATCGTCATAAATATTCAGAATTTG |
| 3. | CAATAGAAAGGGCGACATTAACTGT |
| 4. | CGAAAGAAGGCTTTGAGGAGCACAG |
| 5. | GCCCGAAATTGCATTGGAAGTGCGA |
| 6. | TACCTTTTTACATTACAAACATACC |
| 7. | ATTATCAGGAATTATCATCGTTGCCTTA |
| 8. | CAGACGAGCATTGAAGAACCAATGAAAC |
| 9. | GAAAAGAAATCCAATCGCAGCCAGGTT |

Staple List:

Center staples-those which do not come in contact with the edges of the nanostructure

| SEQ ID NO | SEQUENCE |
|---|---|
| 10. | GCATGATCAAGAAAATTGAGTAAAATAG |
| 11. | GCTATAATGCAGTACGGATTTGGGCAAT |
| 12. | GGGTTATACCTACCATATCAGAAGTTTG |
| 13. | TCCGCGACATCGCCACCTTATAGGACGT |
| 14. | TTTGTCAGGCAACAACGTAGAGCAACTG |
| 15. | ATACGTTTTAGCGAACCGAACGCCTACGCAT |
| 16. | TTTCCTTGAAAACAGTCAATAGTGAAGAGTGTAAC |
| 17. | TAAATCATCCAGTTTGGAAGCGCCAGGGAGCTGATTAT |
| 18. | CCCTCAAGACGGAATAGGTGTAAAAGAAGGCACCAGTAA |
| 19. | GATTATACATTAAAAATACAACGAACCGTCTATCAATCA |
| 20. | AAAAGCGGTTACCAGAAGGAAAGCAGATACCGAAGTTATCCC |
| 21. | AAGTTTACCAGACGCAAAAGAAGTTTGTGCAGACGGTCGAAA |
| 22. | AATTGGGCTTAGAAACATCAGTGAAAATCAAGACAAGACAAT |
| 23. | ACAAATGAATAACAGCTGCTTGCTACCAGTCGCGATTTCTTT |
| 24. | ACTAAGGAATAACTAATGTTGAGAAATATATATACATTAATA |
| 25. | ATGAAAATAAGGTAACCCACAAGACAATGAAATAGCTGAATT |
| 26. | CATCGTATAGCACCATTACCAAGCCAGCCCGACTTAATACCC |
| 27. | CCAGCTACAAGTCTTTCCATAATGGGATAGGTGCATCTGCAC |
| 28. | CTGTTTACTCAACAGTAGGGCAACAGTATAAAGCCGAAAACT |
| 29. | GATGCCAGAGGGGGAATACTGCGGAAGCACGGTGTATCATAA |
| 30. | GCAAATCACATCATTACCGCGCAATAGATAAGTCCCACGCGC |
| 31. | GCGCGAAATTTGACCCCCAGCAAAAAGGCTCCAAAAGGTTGA |
| 32. | GGCTTAAAATTTATCAAAATCATAATCCTGATTCCAGATATT |
| 33. | TGGGATAAAACACTCATCTCATGATACCGATAGCATAATTTT |
| 34. | TTTAATCATAACCGACCGGTAAAGGGCATTTAAACCAAATCA |
| 35. | TTTTCAAACAAGACAAAGAACAAAACAGAAATAAAAGAAAAT |
| 36. | ATACGAGCCGGGAGTGAGAGGTGAGCACGCTGGAAATTGTACA |
| 37. | AATTCATGAGTACAAACGCCTGGCGGGCAACTGGTTTTGCGGTTT |
| 38. | ATATCAATCAAAAAACATTCGCGTCCAATAGAGCTTTCATAGCAA |
| 39. | CCACCACCACCGGAATCCAAAAAGGGTCTTTACCCTGATCCATAA |
| 40. | GAATACACTAACGCCAAATCATAACCCTCTTTGATAAAATACCAA |
| 41. | TATTTGCAGAAGATAAAACAGCTCGAACGAACCACTTGCATGCCC |
| 42. | TTCTGCCGCCTCCCTCAGCCACCACCCTCATTCAAAGCAGAGGAA |
| 43. | AAATCTCGCGTAACGATCTAAAGACAGCTGAGTTTCGTCACCCTAA |
| 44. | ACCGTCAAAAATCACCAAGCAATAAAGCAAACATTTAGCTATGCTG |
| 45. | CGCCACCCAGGAGGTTGCTCCTTTTGATAATTGCTCATCCAAATTC |

-continued

Staple List:

Center staples-those which do not come in contact with the edges of the nanostructure

| SEQ ID NO | SEQUENCE |
|---|---|
| 46. | CTATCTTAGCCGAACATGAGAGTCTGGAAAACTAGCAACCCGATCA |
| 47. | TGTTTCCAACCTGTCTCACATAATATCACCAGCAGTTGAATATACC |
| 48. | AATAAATACAAACAACCGATTGAGATTAAAGGTGAAGATAATAGTTATT |
| 49. | ACAGTTTGAGGCACTCCAGCCTCCCGACTTGTTGCTATTTTGCCATTAA |
| 50. | AGAGAGCCGCTTGCCTTTAGCGTAAGATAGCAGCACCGATTATTCGGAG |
| 51. | CCGACAATATTCGGTATTAAAATCGGCAAAATCCCCCCAGCATCAGCAG |
| 52. | GTAATATATTTGGTTTGTTAATTGATTTAGGTGAACAATGTAGAAAGAT |
| 53. | TTGGTGAGAAGCTACAGCAGCATCCCACGCTGGTTTGCCTTCACCAATT |
| 54. | CAAGAAAAATCTACTACAGGTTTGCTTCTTAAAAGTTTGACACAACTCGTCCTAAA |

Right edge staples-those which come in contact with the right edge (when visualized in cadnano) of the nanostructure; helix ends contain TT overhangs to prevent nanostructure aggregation

| SEQ ID NO | SEQUENCE |
|---|---|
| 55. | TTGACTACCTTTTTAACCTCC |
| 56. | TTATGAACGGTCCCGGTTGATT |
| 57. | TTTCATTACCCATAAGGCTTTT |
| 58. | TTAACCACCAGAGCCCGAGATT |
| 59. | TTGGGCGCATCCGACAGTATTT |
| 60. | TTCCACGCATAAGTTAAAGGTT |
| 61. | TTGCTCATTATTTCGAGGTGTT |
| 62. | TTTTAAATATGCATATAACATT |
| 63. | TTCGGCCTCAGGCTTCTGGTTT |
| 64. | TTTAATCAGAAATATTTAAATT |
| 65. | TTAATTTCTTATTTCTGTATTT |
| 66. | TTTAATTTCAATAAGAACTGTT |
| 67. | TTAAATCGGTTTGCGGGAGATT |
| 68. | TTTAAGACGCTGAACAAAGATT |
| 69. | TTGCCCTGACGGAGATGGTTTT |
| 70. | TTAACGGAACAAACCATCGCTT |
| 71. | TTGTTGATTCCACCGGATATTT |
| 72. | TTAGCCTTTATCATATATTTTT |
| 73. | TTGGATGGCTTCAACATGTTTT |
| 74. | TTACGGCCAGTAGGATCCCCGGGTT |
| 75. | TTGGGATTTTGAGTACAAACTACTT |
| 76. | TTTGTACCAACTCAGAGCATAAAGCTTT |
| 77. | CGAGTAACCGTCACGTTGGTGTAGATTT |
| 78. | AACACATTATGTTAATAAAACGAACTTT |
| 79. | TACAATCGTAGCAAACAAGAGAATCGTT |

-continued

Staple List:

Center staples-those which do not come in contact with the edges of the nanostructure

| SEQ ID NO | SEQUENCE |
|---|---|
| 80. | TTACAACATGTTCAGAGAACAAGCAATT |
| 81. | TTGAAGCAAAGCGGAGACTTCAAATATT |
| 82. | TTTTGTATCGGTTTACAAAGTACAACTT |
| 83. | TTTTTGAAAGAGGACTGGCTGACCTTTT |
| 84. | TTGGACTCCAACGTATCAGATGATGGTT |
| 85. | TTGCCGTTTTATTTTGTTAAATCAGTT |
| 86. | TTTAGGGTTGAGTGTTGTAAAGAATAAGG |
| 87. | TTTCAACCGTTCTATTTTGAGAGATCTT |
| 88. | TTCTAAAACATCGCCTTCTGAATAATTT |
| 89. | TTTTTCCAGACGTTAGGAGCCTTTAATT |
| 90. | TTGGAGATTTGTATCCTGCTCCATGTTT |
| 91. | TTCATCAAGAGTAACTATTATAGTCATT |
| 92. | TTAAATGCTGATGCCCTGTTTAGTATTT |
| 93. | TTTACTTAGCCGGAGAACTGACCAACTT |
| 94. | TTTTCGCAAATGGTGCGCGAGCTGAATT |
| 95. | TTAAGGTGGCATCATAAATCATACAGTT |
| 96. | TTTCGCGTTTTAATACTCCAACAGGTTT |
| 97. | TTTAGCCAGCTTTCTCGGATTCTCCGTT |
| 98. | TTCATATGCGTTATCGACGACAATAATT |
| 99. | TTCAATTCATCAATATAGGTCTGAGATT |
| 100. | TTGGAAGGGTTAGAATAACTATATGTTT |
| 101. | TTACGTTATTAATTTGTAAATCGTCGTT |
| 102. | TTGGTGGTTCCGAATCCTTTGCCCGATT |
| 103. | TTCTCATTTTTAACTGGCCTTCCTGTT |
| 104. | TTAAGATTTAGTTTGACCATTAGATACATTT |
| 105. | AGCTTTTGCGGAGAAGATAGCGATAGCTTAGATTT |
| 106. | TTCCGCTTTTGCGGGATCTGCAGGGACCGATATGAC |
| 107. | TTAACGCCTGTAGCATTCCACAGTTTTGTCGTCTT |
| 108. | TTGCCGGAAACCAGGCCACGGCACCGAAGATCGGGA |
| 109. | TTTTGTAAACGTTAATATTAAGCAAAAGCCCCTATG |
| 110. | TTTACCGAGCTCGAATTCGTAGAACTGATAGCCTT |
| 111. | TTTAAATGCAATGCCTGAGAACCCTTTCAACGATAC |
| 112. | TTCAAGGCGATTAAGTGTGCAGGGGGATGTGCTGTT |
| 113. | TTCATTCAGGCTGCGCAACCAAAGCGCCATTCGCTT |
| 114. | TTGTTTTCCCAGTCACGCACTGGGTAACGCCAGGTT |
| 115. | TACCCCTGTACAAGGATTACACCATCAATATGATATTT |

Staple List:

Center staples-those which do not come in contact with the edges of the nanostructure

| SEQ ID NO | SEQUENCE |
|---|---|
| 116. | TTCGCCAGCTGGCGAAGAAACCTCTTCGCTATTATT |
| 117. | TTGCGATCGGTGCGGGCGTCAACTGTTGGGAAGGTT |
| 118. | TGGCAGGTCGACTCTAGGCCAAGCCAGACGTTGTAAAACGTT |
| 119. | TTTGGGAACAAACGGCGGATTGACCGGACGAGTAACAAATAG |
| 120. | TTTACAAAGGCTATCAGGTCATTGCCAAGAGAGGGATTTATC |
| 121. | TTGCAAGGCAAAGAATTAGCAAAATTAGGCATTAAGAAGAGC |
| 122. | TTCAGGATTAGAGAGTACCTTTAATTGACAGACCGGAAGCAATCGA |
| 123. | TTCACTAACTTTCATGAGGCTGTCACCCGGCGAAAATCCTGTTTGATTT |
| 124. | TCTTTCATTCCAACTAATGTAGCTAGAGCTTAAGAGGTCATTTTTGCTT |
| 125. | CCTGATTCAAAGGGCGAAATGGGCAAGAGTCCACTATTAAAGAACGTTT |
| 126. | TTCTATTAATTAATTTTCCCTTAGAACAAATAACCAGAAAGAGCTTGCG |
| 127. | TGAACACATATCAGAGAGAAATAAAGGTCATAAAGATTCAAAAGGGTGAGAAAGTT |

Left edge staples-those which come in contact with the left edge (when visualized in cadnano) of the nanostructure; helix ends contain TT overhangs to prevent nanostructure aggregation

| SEQ ID NO | SEQUENCE |
|---|---|
| 128. | TTACCACATTCTACGAGGCATT |
| 129. | TTATTAAACGGACCTAAAACTT |
| 130. | TTAGGAGGTTTAGTACCGCCA |
| 131. | TTGTAGCAACGTAGAAAGGATT |
| 132. | TTTTCTAAGAAATAACATAAAAATT |
| 133. | TTGCATTTTCGGTCATAATCAAATT |
| 134. | TTACCAACGCTTTACAAAATAAATT |
| 135. | TTCTAACAACTTGAGGATTTAGATT |
| 136. | TTCAGTGAGACCCTGAGAGAGTTTT |
| 137. | TTAATCAACAGTTGTTAGGAGCATT |
| 138. | TTCAGCCATATTATCCCTTTTTATT |
| 139. | TTCTTAAATCAATTTTTTGTTTATT |
| 140. | TTCCGCCTGCAAAAATCTAAAGCTT |
| 141. | TTAGTACATAAATCTTTAGGAATTT |
| 142. | TTGCAGCAAGCGGTGGAACGAGGTT |
| 143. | TTACAGAATCAAGTCACCCTCAGTT |
| 144. | TTAGACTGGATTCGGAACCTATTTT |
| 145. | TTTTGACGGAATAATCAGTAGCGTT |
| 146. | TTCCGCCGCCATTGGCCTTGATATT |
| 147. | TTTAGTAAGAGATAAGTGCCGTCTT |
| 148. | TTCAATAATAACGGGAGCCATTTTT |
| 149. | TTCAAATGCTTGCCTTGAGTAACTT |

Staple List:

Center staples-those which do not come in contact with the edges of the nanostructure

| SEQ ID NO | SEQUENCE |
|---|---|
| 150. | TTGAAACGTCACCACCACCAGAGTT |
| 151. | TTAACCGCCACGAAAGCGCAGTCTT |
| 152. | TTTTACGCAGTATGAGGTAAATATT |
| 153. | TTTAGCGAGAGCTCAAGAGAAGGTT |
| 154. | TTGGGTAATTGGAAACGCAAAGATT |
| 155. | TTACAACGCCAAGTAATAAGAGATT |
| 156. | TTCAGGGAAGCGCAAAAGTCAGATT |
| 157. | TTGAAAGAGGCATCACCGTACTCTT |
| 158. | TTCCAGCGCCAGCGTTTTCATCGTT |
| 159. | TTAGTATTAGACTTGAAGTTTCCTT |
| 160. | TTCACCACGGAATATATGGTTTATT |
| 161. | TTTCCTAATTTGTCTTTCCTTATTT |
| 162. | TTGCGCGGGGAGAGTCTTTTCACTT |
| 163. | TTAGAAAAGTAACCGAGGAAACGTT |
| 164. | TTCAAAATTAATTTAATGGAAACTT |
| 165. | TTTAACGTCAGGGAGAAACAATATT |
| 166. | TTATTCATTTCAATTCAAGAAAATT |
| 167. | TTGGGAATTAGTTAGCAAGGCCGTT |
| 168. | TTACGTCAAAAATGTAAGCCCAATT |
| 169. | TTGCCTGGGGTGTTGCGCTCACTTT |
| 170. | TTATCACCGGATTTTGATGATACTT |
| 171. | TTACAACTAAACTCAGAACCGCCTT |
| 172. | TTTCTGACCTAAAATAAGGCGTTTT |
| 173. | TTTAATAAGAGTAAGACTCCTTATT |
| 174. | TTACGGATTCGCCTCAGAGGCGAATTTT |
| 175. | TTGCCCGCTTTCCAGAATCGGCCAACTT |
| 176. | TTATCACCTTGCTGGGTCAGTTGGCATT |
| 177. | GCCTATTAGCGTCCTAATAGTAAAATGTTTTT |
| 178. | GGTCAGTTAAACAGTTCATTGAATCCCCCTTT |
| 179. | GAGACTCGCTTTTGACGATAAAAACCAAAATT |
| 180. | TTTTATCCGCTCACAATTCCACACAATGTCATAGC |
| 181. | TTATTCTGAAACATGAAAGTATTAAGCAACCCCCT |
| 182. | TTTTCACAAACAAATAAATCCTCATTACGGCAGGT |
| 183. | TTAGGAGTGTACTGGTAATAAGTTTTCAATGTCAT |
| 184. | TTATTAGGATTAGCGGGGTTTTGCTCGTGTAGGCT |
| 185. | TTAGTGCCCGTATAAACAGTTAATGCAGATAACGG |

Staple List:

Center staples-those which do not come in contact with the edges of the nanostructure

| SEQ ID NO | SEQUENCE |
|---|---|
| 186. | TTTGTAACACCCTCATAGTTTCAGGGATAGCAAGCCTT |
| 187. | TTCAATAGGAACCCATGTACCCAGCGGACGAATAACTAC |
| 188. | GATAATATCTAAAGGAACATTAATGTCGGGATGTGTGAAATTGTT |
| 189. | CAGCCCATGAAATAAGAAACGAGATTAGCGGGAGGTTTTGAAGCTT |
| 190. | AATCCAGGCCTAATTTGCCAGAACGAGCTTTTATCCTGAATCTTTT |
| 191. | AATCGCGGATTGCTCAAATGAACAGTGCGCGGTCAGTATTAACATT |
| 192. | TTACCCTCAGAGCCACCACCCTCATTTACAAGAACCGCCACCGGAA |
| 193. | TTTCTGAATTTACCGTTCCAGTAAGCTAGAAAAGCCAGAATGCCTC |
| 194. | TTGAGAGGGTTGATATAAGTATAGCCTTTTAGTACCAGGCGGCAAC |
| 195. | TGAAATATCTAACCTCATAATTGCGCCTAATAAGCATAAAGTGTAAATT |
| 196. | ATAGGAGAATATTTTACAGAGAGACGCGAGGGAAGGCTTATCCGGTATT |
| 197. | CTACCTGAACTTAGACGATCGGCTACGAGCAGAAAAATAATATCCCATT |
| 198. | TTAAATAAGAATAAACACCGGTACATCGATGAATACGTAGATTTTCAGGTTTT |
| 199. | TTATATAAAGTACCGACAAAAGTGTGATAATTTAATTAGTTAATTTCATCTTT |
| 200. | TTCATTCCAAGAACGGGTATTTCGAGCCACATGTAAGAATCGCCATATTTATT |

Cavity staples-those which protrude into the cavity of the nanostructure exposing AAAAAAAAAAAAAA (SEQ ID NO: 217) handles

| SEQ ID NO | SEQUENCE |
|---|---|
| 201. | AACATTTTTAGTAATGTGTAGGATGAAAAAAAAAAAAAAA |
| 202. | CGAATAGATAGTGAGTGTTTGAATGAAAAAAAAAAAAAAA |
| 203. | CTAATAGAGCCTGATGAATAACAATGAAAAAAAAAAAAAAA |
| 204. | ACATGGCACCAGAGTCTTTTCATAGCCCGAAAAAAAAAAAAAAA |
| 205. | GACTTTTACGTAATTTCATCAGCAGATAGAAAAAAAAAAAAAAA |
| 206. | GGGAACCACGAGGCAGTAAATCATTGTGGAAAAAAAAAAAAAAA |
| 207. | ACTCATCGCTAATGCAGAAGATAATTCTCAAAAAAAAAAAAAAA |
| 208. | GTCCAGAACAAATTCTTACATATTACTACAAAAAAAAAAAAAAA |
| 209. | TAAATTTTTCATCGTAGGACAGTACCGCGAAAAAAAAAAAAAAA |
| 210. | ACGAGTAGCGAACGAGAATGACTTCGTAACAGAAAAAAAAAAAAAAA |
| 211. | GCGTATTCCAGCTGTTGAGGACTCAATCGCAAAAGGTTACAAGAAAAAAAAAAAAAAA |
| 212. | ATCAAAACCAGGCGCATAGGCAGATGATGCTCATCCAGAACCAAAAAAAAAAAAAAA |
| 213. | CCTTATTGCTCAGACTGTAGCAAGACAAAAATTCAAGTTTATGAAAAAAAAAAAAAAA |
| 214. | TTGCCGGAGACAGTCAAATCAGATTGTATTTGTTAAAATTACGAAAAAAAAAAAAAAA |

Cavity binding oligo

| SEQ ID NO | SEQUENCE |
|---|---|
| 215. | /5Hexynyl/TTTTTTTTTTTTTT |

Loop binding oligo

| SEQ ID NO | SEQUENCE |
|---|---|
| 216. | /5Alex647N/TGAGTAGAAGAACTCAAACTATCGGCCTTGCTGGTAATAT |

REFERENCES

1 Griffin, D. R. & Kasko, A. M. *Photodegradable Macromers and Hydrogels for Live Cell Encapsulation and Release. J. Am. Chem. Soc.* 134, 13103-13107 (2012).
2 Deng, L., Norberg, O., Uppalapati, S., Yan, M. & Ramstrom, O. Stereoselective synthesis of light-activatable perfluorophenylazide-conjugated carbohydrates for glycoarray fabrication and evaluation of structural effects on protein binding by SPR imaging. *Org. & Biomol. Chem.* 9, 3188-3198 (2011).
3 Hong, V., Presolski, S. I., Ma, C. & Finn, M. G. Analysis and Optimization of Copper-Catalyzed Azide-Akyne Cycloaddition for Bioconjugation. *Angew. Chem. Int. Ed.* 48, 9879-9883 (2009).
4 Douglas, S. M. et al. Rapid prototyping of 3D DNA-origami shapes with caDNAno. *Nucleic Acids Res.* 37, 5001-5006 (2009).
5 Sambrook, J. Molecular Cloning: A Laboratory Manual. 3rd ed. edn, (Cold Spring Harbor Laboratory Press, 2001).
6 Stahl, E., Martin, T. G., Praetorius, F. & Dietz, H. Facile and Scalable Preparation of Pure and Dense DNA Origami Solutions. *Angew. Chem. Int. Ed.* 53, 12735-12740 (2014).

Example 2—Oligonucleotide

FIG. 10 A shows the structure of glutamate-linker-oligonucleotide conjugate, prepared as in Example 1. The oligonucleotide is SEQ ID NO: 215.

FIG. 10B shows normalized fluorescence intensity of the calcium indicator Fluo-4 in two neurons in the presence of glutamate-linker-oligonucleotide. One second of light irradiation initiated cleavage of the linker and release of glutamate, which caused an increase in intracellular calcium. The two traces indicate calcium signals from two different neurons. Neurons were prepared as in Example 1. Imaging was performed with a wide-field Olympus IX81 inverted microscope. 15 seconds after the start of the recording, DAPI filter cube was used to illuminate neurons with long wave UV (centered around 365 nm) for 1 second, before returning to imaging of Fluo-4. During the exposure of UV light, the florescent intensity of Fluo-4 was not recorded.

Other embodiments are in the claims.

What is claimed is:

1. An oligonucleotide conjugate of the formula:

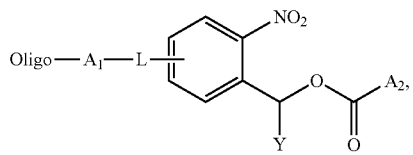

wherein Oligo is an oligonucleotide of 2-1000 nucleotides in length, Ai is the residue of a conjugation reaction, $A_2$ is an amine reactive leaving group or —NHX, L is an optional linker, Y is H or C1-10 alkyl, and X is a cargo moiety.

2. The conjugate of claim 1, wherein L is present and amido, C1-10 alkylene, or C1-20 polyalkeneoxide.

3. The conjugate of claim 1, wherein L is present and C2-C20 polyethylene glycol.

4. The conjugate of claim 1, wherein Ai is triazolyl, disulfide, cyclohexenyl, amido, thioamido, acetal, ketal, or sulfonamido.

5. The conjugate of claim 1, wherein Y is C1-10 alkyl.

6. The conjugate of claim 1, wherein Y is methyl.

7. The conjugate of claim 1, wherein $A_2$ is the amine reactive group.

8. The conjugate of claim 7, wherein the amine reactive group is p-nitrophenoxyl, N-hydroxysuccinimidyl, halide, pentafluorophenoxyl, or imidazolyl.

9. The conjugate of claim 1, wherein $A_2$ is NHX.

10. The conjugate of claim 9, wherein X is a therapeutic or diagnostic agent.

11. The conjugate of claim 1, having the formula:

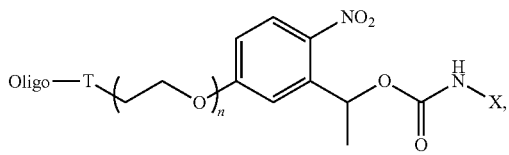

wherein Oligo is an oligonucleotide of 2-100 nucleotides in length, T is a triazolyl linker formed from the reaction of an azide with an alkyne, X is a cargo moiety, and n is an integer from 1-10.

12. A crosslinker of the formula:

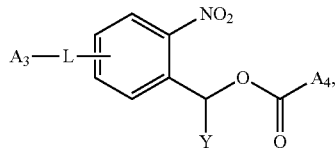

wherein $A_3$ is a conjugating moiety, $A_4$ is an amine reactive leaving group, L is C2-C20 polyethylene glycol, and Y is H or C1-10 alkyl.

13. The crosslinker of claim 12, wherein $A_3$ is azido, alkynyl, alkenyl, thiol, halide, boronic acid, hydroxyl, carboxyl, formyl, or ketone.

14. A crosslinker of the formula:

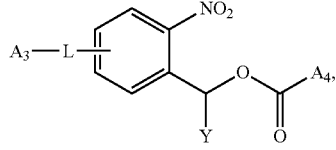

wherein $A_3$ is a conjugating moiety, $A_4$ is an amine reactive leaving group, L is an optional linker, and Y is C1-10 alkyl.

15. The crosslinker of claim 14, wherein Y is methyl.

16. The crosslinker of claim 12, wherein $A_4$ is p-nitrophenoxyl, N-hydroxysuccinimidyl, halide, pentafluorophenol, or imidazolyl.

17. The crosslinker of claim 12, having the formula:

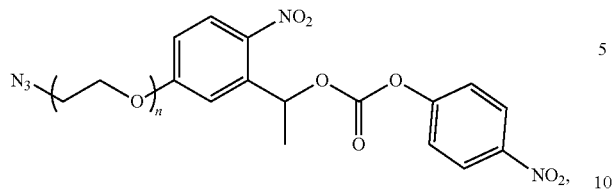

where n is an integer from 1-10.

18. A DNA construct comprising a three-dimensional DNA cage structure for housing a cargo moiety, wherein the cargo moiety is attached to the cage structure via the oligonucleotide conjugate of claim 1.

19. A method of delivering a cargo moiety, the method comprising providing a conjugate of claim 1 and irradiating the conjugate with light to release the cargo moiety.

20. The method of claim 19, wherein the conjugate is internalized within a cell prior to irradiation.

21. The method of claim 19, wherein the cargo is a therapeutic or diagnostic agent.

22. A pharmaceutical composition comprising a conjugate of claim 1 and a pharmaceutically acceptable carrier.

23. The crosslinker of claim 14, wherein $A_3$ is azido, alkynyl, alkenyl, thiol, halide, boronic acid, hydroxyl, carboxyl, formyl, or ketone.

24. The crosslinker of claim 14, wherein $A_4$ is p-nitrophenoxyl, N-hydroxysuccinimidyl, halide, pentafluorophenol, or imidazolyl.

* * * * *